US009624292B2

(12) United States Patent
Voss et al.

(10) Patent No.: US 9,624,292 B2
(45) Date of Patent: Apr. 18, 2017

(54) SINGLE CHAIN ANTIGEN RECOGNIZING CONSTRUCTS (SCARCS) STABILIZED BY THE INTRODUCTION OF NOVEL DISULFIDE BONDS

(75) Inventors: Ralf-Holger Voss, Ingelheim (DE); Shao-An Xue, London (GB); Matthias Theobald, Mainz (DE); Hans Stauss, London (GB)

(73) Assignee: Universitätsmedizin Der Johannes Gutenberg-Universität Mainz, Mainz (DE)

( * ) Notice: Subject to any disclaimer, the term of this patent is extended or adjusted under 35 U.S.C. 154(b) by 743 days.

(21) Appl. No.: 14/006,254

(22) PCT Filed: Mar. 26, 2012

(86) PCT No.: PCT/EP2012/055343
§ 371 (c)(1),
(2), (4) Date: Jan. 10, 2014

(87) PCT Pub. No.: WO2012/127063
PCT Pub. Date: Sep. 27, 2012

(65) Prior Publication Data
US 2014/0112925 A1    Apr. 24, 2014

(30) Foreign Application Priority Data
Mar. 24, 2011 (EP) .................................... 11159650

(51) Int. Cl.
*C12N 5/0783*    (2010.01)
*C07K 16/00*    (2006.01)

(52) U.S. Cl.
CPC ........ *C07K 16/00* (2013.01); *C07K 2317/624* (2013.01)

(58) Field of Classification Search
None
See application file for complete search history.

(56) References Cited

U.S. PATENT DOCUMENTS 6,147,203 A    11/2000    Pastan et al.

FOREIGN PATENT DOCUMENTS

WO    WO 2006/103429 A2    10/2006
WO    WO 2007/109254 A2    9/2007
WO    WO 2010/026377 A1    3/2010

OTHER PUBLICATIONS

Cai, Kun et al., "Novel human 3-domain disulfide-stabilized antibody fragment against glycoprotein of rabies virus," *Microbes and Infection*, 2008, vol. 10, p. 548-555.
Chung, Shan et al., "Functional three-domain single-chain T-cell receptors," *Proceedings of the National Academy of Science*, USA, Dec. 1994, vol. 91, p. 12654-12658.
Luo, Dong et al., "Vl-Linker-Vh Orientation-Dependent Expression of Single Chain Fv Containing an Engineered Disulfide-Stabilized Bond in the Framework Regions," *Journal of Biochemistry*, 1995, vol. 118, p. 825-831.
Marcu-Malina, Victoria et al., "Re-targeting T-cells against cancer by gene-transfer of tumor-reactive receptors," *Expert Opinion on Biological Therapy*, 2009, vol. 9, No. 5, p. 579-591.
Raats, Jos et al., "Recombinant antibody expression vectors enabling double and triple immunostaining of tissue culture cells using monoclonal antibodies," *European Journal of Cell Biology*, 2005, vol. 84, p. 517-521.
Rajagopal, Vivek et al., "A form of anti-Tac(Fv) which is both single-chain and disulfide stabilized: comparison with its single-chain and disulfide-stabilized homologs," *Protein Engineering*, 1997, vol. 10, No. 12, p. 1453-1459.
Shusta, Eric et al., "Directed evolution of a stable scaffold for T-cell receptor engineering," *Nature Biotechnology*, Jul. 2000, vol. 18, No. 7, p. 754-759.
Voss, Ralf-Holger et al., "Coexpression of the T-cell receptor constant α domain triggers tumor reactivity of single-chain TCR-transduced human T cells," *Blood*, 2010, vol. 115, p. 5154-5163.
Wörn, Arne et al., "Stability Engineering of Antibody Single-chain Fv Fragments," *Journal of Molecular Biology*, 2001, vol. 305, p. 989-1010.
Young, N. Martin et al., "Thermal stabilization of a single-chain Fv antibody fragment by introduction of a disulphide bond," *FEBS*, 1995, vol. 377, p. 135-139.
Zhao, Jian-Xin et al., "Stabilization of the Single-Chain Fragment Variable by an Interdomain Disulfide Bond and Its Effect on Antibody Affinity," *International Journal of Molecular Science*, 2011, vol. 12, p. 1-11.
Robinson, C.R., Sauer, R.T., "Optimizing the stability of single-chain and composition mutagenesis." *Proc. Natl. Acad. Sci. USA* 95:5929-5934, May 1998.
Schimmele, B., Plückthun, A., "Engineering Proteins for Stability and Efficient Folding." *Protein Science Encyclopedia—Online*, 2005, pp. 1-53; DOI: 10.100/9783527610754.

*Primary Examiner* — Zachary Skelding
(74) *Attorney, Agent, or Firm* — Saliwanchik, Lloyd & Eisenschenk

(57) ABSTRACT

The present invention relates to a single chain antigen recognizing construct (scARC), which is composed of stabilized variable domains by the introduction of novel disulfide bonds, in order to prevent residual mis-pairing with endogenous ARC chains. The invention further discloses a method for the design of a novel structurally stabilized scARC, the method being based on the visual inspection of the crystal structure of the underlying scARC and the selection of appropriate amino acid substitutions to generate a novel disulfide bond in the protein structure. Furthermore, the invention discloses a method for the production of a cell which expresses the scARC of the invention. Also described are nucleic acids encoding an inventive scARC, as well as DNA and RNA constructs that allow for the expression of the inventive scARC. The invention further encompasses pharmaceutical compositions containing the scARC of the invention and the use of the scARC in therapy of cancerous or infectious diseases, or for use in the quantification and/or visualization of disease associated antigens.

10 Claims, 16 Drawing Sheets

Figure 1:
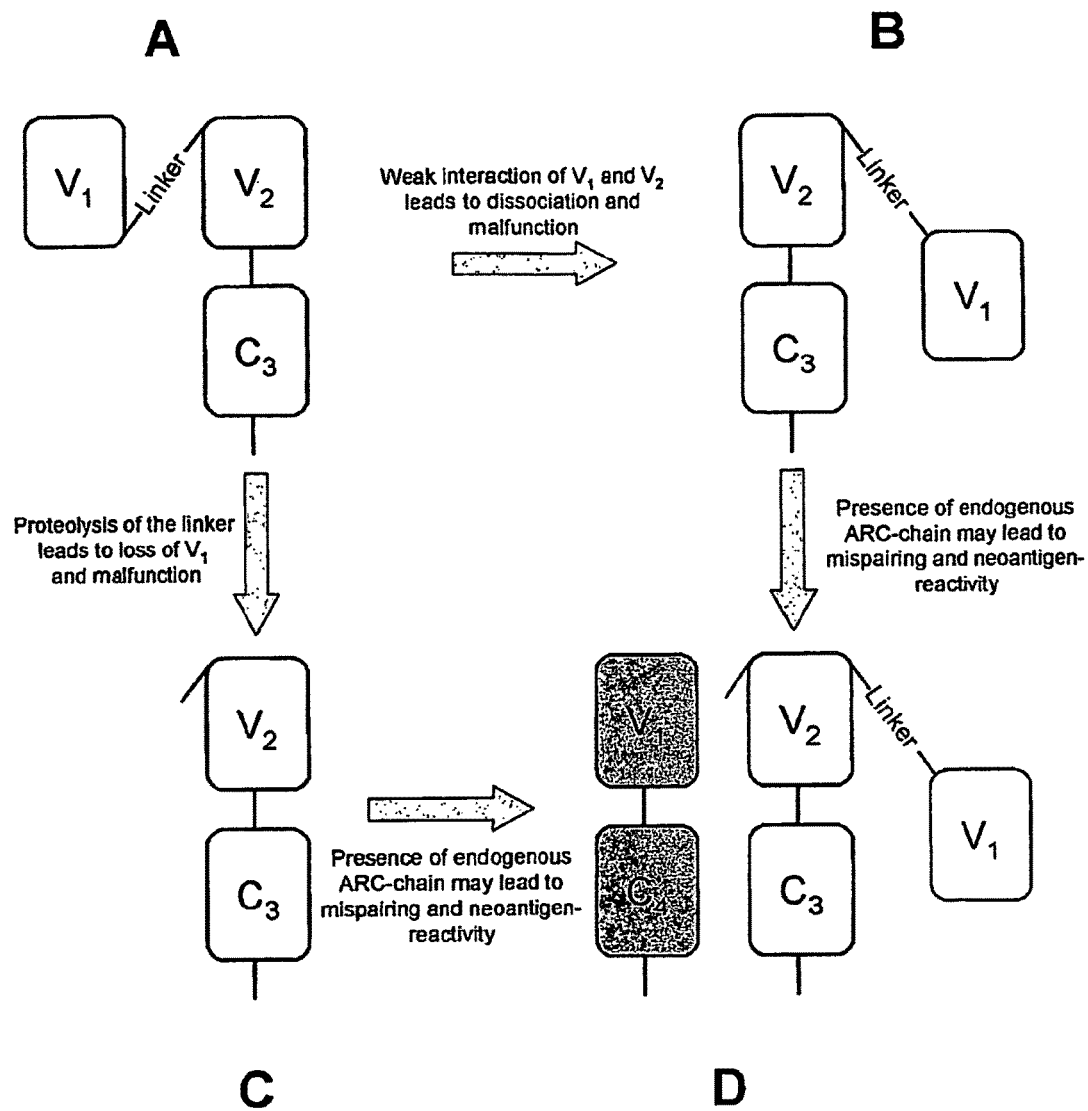

Reference

SINGLE CHAIN ANTIGEN RECOGNIZING CONSTRUCTS (SCARCS) STABILIZED BY THE INTRODUCTION OF NOVEL DISULFIDE BONDS

CROSS REFERENCE TO A RELATED APPLICATION

This application is a National Stage Application of International Application Number PCT/EP2012/055343, filed Mar. 26, 2012; which claims priority to European Patent Application No. 11159650.8, filed Mar. 24, 2011; which are incorporated herein by reference in their entirety.

FIELD OF THE INVENTION

The present invention relates to a single chain antigen recognizing construct (scARC), which is composed of stabilized variable domains by the introduction of novel disulfide bonds, in order to prevent residual mis-pairing with endogenous ARC chains. The invention further discloses a method for the design of a novel structurally stabilized scARC, the method being based on the visual inspection of the crystal structure of the underlying scARC and the selection of appropriate amino acid substitutions to generate a novel disulfide bond in the protein structure. Furthermore, the invention discloses a method for the production of a cell which expresses the scARC of the invention. Also described are nucleic acids encoding an inventive scARC, as well as DNA and RNA constructs that allow for the expression of the inventive scARC. The invention further encompasses pharmaceutical compositions containing the scARC of the invention and the use of the scARC in therapy of cancerous or infectious diseases, or for use in the quantification and/or visualization of disease associated antigens.

BACKGROUND OF THE INVENTION

Antibodies and T-cell receptors (TCR) are the two key molecules of the adaptive immune system in vertebrates having the unique ability to bind and recognize specific structural elements—so called antigens. Antibodies and TCRs are members of the immunoglobulin superfamily of proteins, a family which is characterized by the presence of an immunoglobulin domain or fold in their 3-dimensional protein structure. Antibodies are usually produced by blood cells in either soluble or membrane bound form (B-cell receptor) and aid the immune system in the detection and targeting of potentially pathogenic structures within the host organism—usually structures of pathogenic organisms like bacteria or viruses. TCRs on the other hand are expressed on T-cells and mediate the recognition of antigens presented by the major histocompatibility complex (MHC), among many others antigens which are specific for tumor cells. Due to their key function in the host's detection of potential threads, they are central in the development of immune system based therapeutics for the treatment of many diseases including cancerous and infectious diseases.

The T cell receptor is expressed on the cell surface of T cells as part of the adaptive immune system and is capable of recognizing peptide antigens presented on MHC class I and II molecules. The binding of the cognate antigen is followed by a cytolytic or cytokine secretion response, respectively, that promotes the elimination of cognate antigen presenting cells. In immunotherapy, this strategy may be employed to eradicate aberrant cells that present tumor associated antigens to cure cancer diseases (Rosenberg et al., 2008). Under certain circumstances, tumor-reactive T cells will not be identified in tumor patients due to functional unresponsiveness or low T cell frequencies. In order to circumvent central and peripheral tolerance mechanisms one aims at providing tumor-reactive high-affinity (TCRs) by genetic reprogramming of the patient's T cells. For this, the TCR encoding sequences are cloned into an e.g. retroviral shuttle vector. The cells are isolated from peripheral blood and treated with the retro:virally recombinant particles harvested from the supernatant of a producer packaging cell line. The heterologous expression of this TCR can be monitored by flow cytometry analysis. Afterwards, the reprogrammed autologous T cells are expanded short-term ex vivo and eventually are adoptively transferred to the patient. This therapeutical concept proved to be effective in the regression of progressive cancer diseases in few clinical trials recently (Johnson et al., 2009).

However, the T cell receptor consists of an αβ-heterodimer each chain comprising the antigen-recognizing variable $V_\alpha$- or $V_\beta$- and a constant $C_\alpha$- or $C_\beta$-domain, respectively, of an immunoglobulin-like fold linked by a natural disulfide bond close to the cell membrane. Both chains recognize specifically the MHC/peptide-complex via their CDR1-3 loops, located on each chain and cumulatively contribute to the affinity of the TCR. The expression of a second TCR in a human T cell may allow for the mixed pairing of exogenous and endogenous TCR chains to produce mis-paired or hybrid TCRs with unforeseen, potentially auto-reactive antigen specificities (Schumacher, 2002). The so-called "off-target"-reactions of reprogrammed T cells could be demonstrated in a mouse model leading to overt auto-immune disease, such as symptoms of so-called graft-versus-host disease (Bendle et al., 2010).

A reasonable strategy is to generate 3-domain single chain TCRs, which harbour covalently linked variable domains, that in theory hardly dissociate and mis-pair (FIG. 1A). The membrane anchoring of $V_\alpha$-Linker-$V_\beta$ is accomplished by a constant $C_\beta$-domain right after the variable $V_\beta$-domain. In the past, this construct turned out to be functional only when the missing $C_\alpha$-domain is co-expressed (DE10259713.8) and when the C-domains were murinized (DE102006041455.1). For this, the immunoglobulin-like folded $C_\alpha$-domain has been modified to a membrane secretion protein by preceding it with a eukaryotic signal peptide (SP) (Voss et al., 2010).

The required murinization of a scTCR- or scCAR-construct coexpressed with a murine Cα-domain strengthen the interaction between the C-domains and thus, the stability of the TCR or CAR-construct. The classical scTCR or scCAR-scaffold, that is based on the fusion of the CD3ζ-signaling domain at the expense of Cα does not require murinization. The novel disulfide bonds may be applied to both strategies in order to improve the stability of the variable scTCR- or scFv-fragment. Due to structural homology of αβTCRs and γδTCRs, the same disulfide bonds may also be applied to stabilize scTCR-fragments of a γδTCR. In the meantime minimal murinization strategies allow for the substantial reduction of xenogeneic moieties to avoid immunogenic reactions against the chimeric molecule (Bialer et al., 2010; Sommermeyer and Uckert, 2010). For this, 9 murine amino acid residues in Cα and Cβ are sufficient at all to trigger the beneficial effect of stabilizing scTCR or scCAR-expression. Importantly these residues are located at the inner interface of the C-domains and thus, will be hardly accessible to the host immune system, in particular the complement system, to initiate any host versus graft immune response.

In a single or double chain format, antigen-recognizing fragments may also be derived from other species such as rabbit, goat, rat. The V-domains can be almost completely humanized except the sequences CDR1-3 of either chain that are responsible for specific antigen recognition (for example in the known antibody Herceptin®).

The introduction of an artificial disulfide bond at the interface of the C-domains at $C_\alpha$ T84C/$C_\beta$ S79C (Kuball et al., 2007) according to the nomenclature of the IMGT database (Lefranc, 2003; Lefranc et al., 2005) improved expression of the scTCR/$C_\alpha$ scaffold (Voss et al., 2010). Most importantly, this disulfide bond does not affect the interaction strength of the $V_\alpha$/$V_\beta$-domains.

TCR gene therapy is at the beginning of its clinical application and needs further basic research to proceed from "bench to bedside". In experimental and animal models, an alternative strategy to avoid mis-pairing utilizes the i) 4-domain scTCR concept, in that the signalling component CD3ζ including its transmembrane region of the CD3-complex is fused to the aforementioned 3-domain scTCR (Willemsen et al., 2000). However, the coupling to the signalling component CD3ζ may induce its over-expression with unforeseen consequences on antigen specificity and T cell signalling.

Another strategy is to include an artificial disulfide bond, that covalently links the $C_\alpha$- with the $C_\beta$-domain (WO2004/033685). This approach resulted originally from experiments to increase the stability of bacterially expressed soluble double chain (dc) TCRs for protein crystallization (Boulter et al., 2003) and has been generalized to phage display for the isolation of high-affinity tumor-reactive TCR in vitro (Avidex, Abingdon, UK; (Li et al., ZOOS)). Disulfide bridges form lately during the posttranslational modification steps after ribosomal protein biosynthesis in the endoplasmic reticulum. Although dcTCRs pair earlier in the endoplasmic reticulum, the introduction of an artificial disulfide bond in C-domains shifts the equilibrium of chain pairing towards dcTCRs being able to create the cysteine bridge. However, this does not inhibit pairing of exogenous and endogenous chains, due to the stereochemical similarity of serine and threonine. Additionally, cysteine is a rather small polar amino acid that may allow approximation of almost all amino acid residues of the interacting TCR chain.

The introduction of reciprocal mutations, that sustain the steric and electrostatic environment at the interface of constant domains, modified complementarity such that almost exclusively the exogenous TCRs fit together, thereby avoiding the formation of hybrid TCR (Voss et al., 2008). In C-domains reciprocally mutated TCRs are almost as effective as wild type TCRs in effector function in vitro (Voss et al., 2008) and in vivo albeit showing a reduced structural avidity in tetramer analysis. This makes it difficult to monitor and to track them in vivo. Additionally, they do not entirely avoid formation of hybrid TCRs. The potential to avoid mis-pairing probably relates to the intrinsic qualities of TCR subfamilies and CDR3 sequences that contribute to TCR chain pairing (Heemskerk et al., 2007)

Further on, specific pairing of the exogenous TCRs is believed to be improved by the murinization of the constant domains of double chain TCRs (Voss et al., 2006; Cohen et al., 2006). It is shown, that murine constant domains have a higher affinity to each other due to more pronounced basic patches at the interface of $C_\beta$ that binds more strongly to $C_\alpha$ by electrostatic interactions. Recently, it was shown that murinization could be confined to a minimal set of defined residues so as to minimize xenogeneic reactions (Bialer et al., 2010; Sommermeyer and Uckert, 2010). The preferential pairing and thus, themodynamic and proteolytic stabilization of murinized TCRs outcompetes the surface expression of endogenous TCRs since endogenous and exogenous TCRs have to compete for binding to the CD3-complex as a prerequisite for secretion to the cell surface. Additionally, murine constant domains seem to efficiently interact with human CD3 components, as this in general is an elementary step in T cell signaling (Call et al., 2002). However, murine C-domains are still able to pair with endogenous C-domains despite their differences and hence may still lead to unwanted mis-pairing.

The codon-optimization of human and murine TCR substantially increased expression and functionality of heterologously expressed TCR in human T cells. The strategy yielded improved translation due to usage of the most frequent triplets in eukaryots, the adaptation of the GC-content, the elimination of cryptic splice-donor sites in RNA sequences and the avoidance of repetitive sequences, killer motifs and RNA secondary structure ((Jorritsma et al., 20C17); GENEART, Regensburg). However, it is by far not as efficient as murinization of TCRs to outcompete and down-regulate endogenous TCR expression. Additionally, it does not evoke preferential pairing of exogenous TCRs on a molecular basis. Therefore, mis-pairing of TCR chains still occurs.

For a short time, there are efforts to specifically eliminate endogenous TCRs by the digestion of the TCR RNA pool through siRNAs (Okamoto et al., 2009) or to even excise the related genes from the genome by zinc finger nucleases (Sangamo, Richmond, Calif.; (Miller et al., 2007)) Some of these strategies have a minimal impact on TCR structure and immunogenicity and additionally did not yield full knock-out of endogenous TCRs. At present genome editing is at its experimental advent and quite far away from clinical application.

Recent experiments demonstrated that a human WT1 (Xue et al., 2010)—and a CMV-specific scTCR were non-functional although they were designed to be co-expressed with murine $C_\alpha$ the same way as another, fully functional human scTCR gp100 (Voss et al., 2010): They were murinized in C-domains, modified to form the artificial disulfide bond (Kuball et al., 2007) and even codon-optimized (Jorritsrna et al., 2007) to increase expression. Secondly, recent hints indicated that residual mis-pairing with endogenous TCR chains still took place although it was argued in literature (Chung et al., 1994) that this should have been completely avoided by sterical hindrance of the $V_\alpha$-moiety in scTCR-design.

SUMMARY OF THE INVENTION

In view of the state of the art it was an object of the present invention to provide single chain antigen recognizing constructs (scARC) having a stabilized domain structure, particularly in their variable domains, and which are therefore less prone to undesirable residual mis-pairing of the expressed scARC with endogenous ARC molecules, like TCRs or antibody fragments. The present invention further intends to provide novel strategies for the design of any scARC, either antibody-based or TCR-based. Specifically the inventors were prompted to improve the interaction strength of TCR V-domains to make the previously described approaches, in particular the scTCR/$C_\alpha$-approach, broadly applicable to ARC-subfamilies and to abolish residual mis-pairing which might cause severe autoimmune side reactions in patients.

The object of the present invention is solved in a first aspect by providing a stabilized functional single chain antigen-recognizing construct (scARC), comprising the domains $V_{1/2}$-Linker-$V_{1/2}$-$C_{1/2}$, wherein the variable domains $V_1$ or $V_2$ are structurally stabilized by one or more disulfide bonds.

In one embodiment of the present invention the stabilized functional scARC of the present invention comprises the domains $V_1$-Linker-$V_2$-$C_2$ or $V_2$-Linker-$V_1$-$C_1$ or $V_1$-Linker-$V_2$-$C_1$ or $V_2$-Linker-$V_1$-$C_2$.

The object of the present invention is also solved in a preferred aspect by providing a stabilized functional single chain antigen-recognizing construct (scARC), comprising the domains $V_1$-Linker-$V_2$-$C_2$ or $V_2$-Linker-$V_1$-$C_1$, wherein the variable domains $V_1$ or $V_2$ are structurally stabilized by one or more disulfide bonds.

In order to observe the occurrence of mis-pairing with endogenous $TCR_\alpha$ as an undesignated side reaction in vitro, the inventors co-transduced in $TCR_{\alpha/\beta}$-deficient leukemic T-cell-line (Jurkat-76) a murinized scTCR gp100 specific for the gp100(280-288) antigen and the $TCR_\alpha$ gp100-chain of the same specificity. In this model, the latter one served as a mimicry for an arbitrary endogenous $TCR_\alpha$-chain that might interact with the introduced scTCR and thus, resembles the situation in human T-cells. In theory, sterical hindrance mediated by $V_\alpha$ of the scTCR and the missing co-expression of $C_\alpha$ should prevent successful surface expression of the scTCR. It was previously demonstrated that the scTCR is only transported to the cell surface when pairing to the $C_\alpha$-domain is accomplished (Voss et al., 2010). The presence of both $C_\alpha$ and $C_\beta$ provide for the entire assembly of the TCR/CD3 signalling-complex and initiates functionality (Call et al., 2002).

Mis-pairing of scTCR gp100 with $TCR_\alpha$ gp100 was surprisingly observed as read out by TCR- or CD3-surface expression in Jurkat-76 (anti-murine $TCR_\beta$-, tetramer- or anti-human CD3-staining) or cytokine-secretion upon specific antigen-encounter in IFNγ-ELISA down to $10^{-8}$ M peptide. Such mis-pairing is problematic, as proteolysis (FIG. 1C) or dissociation of $V_\alpha$ from $V_\beta$ (FIG. 1B) due to weak interactions may lead to a residual $V_\beta/C_\beta$-architecture that does not recognize it's cognate antigen anymore. Eventually, this may even be followed by mis-pairing with abundant endogenous $TCR_\alpha$ chains in T-cells since the sterical hindrance mediated by $V_\alpha$ is not valid anymore (FIG. 1D). This may provoke neoantigen-recognition and autoimmunity. In one embodiment the present invention therefore seeks to provide a possibility to strengthen the interaction between weak interacting variable domains in a scARC.

Hence, the invention described herein comprises the solution to prevent residual mis-pairing of single chain TCRs, in general termed single chain antigen recognizing constructs (scARC) to include single chain antibody fragments (scFv's; (Maher et al., 2002)) in this concept. The inventors accomplished this by introducing a disulfide bond into the scARC that affects the interaction strength and degree of rotational freedom of $V_\alpha$- and $V_\beta$-domains. The inventors designed a set of disulfide bridges located at different positions of scTCR domains to determine the best cysteine linkage combining optimal and specific functionality with optimized $V_\alpha/V_\beta$-pairing and minimized mis-pairing, respectively. To this end the visual inspection of murine (RCSB entry 1TCR.pdb) or human (2VLM.pdb) TCR high resolution crystal structures were used to detect pairs of amino acid residues that are in a favourable orientation and distance located in or close to the V-domains for being mutated to cysteines that automatically may form a disulfide bond by an appropriate redox potential when exported to the cell surface.

For the purpose of the present invention the designations $V_{1/2}$ or $C_{1/2}$ shall be understood as a generic term for the domain compositions of the herein described ARCs. "V" abbreviates a variable domain, whereas "C" stands for a constant domain. The index "1" designates a variable or constant domain of an ARC selected from an alpha or gamma chain in case of scTCRs, or for a light chain in the case of antibody based constructs like scFv fragments. The index "2" refers respectively to the beta or delta chain in the context of scTCRs and to the heavy chain in an antibody based construct.

Therefore in the context of the present invention, the designation $V_{1/2}$ refers to both, to the commonly used designation $V_{\alpha/\beta}$ (or $V_{\beta/\alpha}$) or $V_{\gamma/\delta}$ (or $V_{\delta/\gamma}$) in the context of T-cell receptors, or to $V_{h/l}$ (or $V_{l/h}$) in the case of antibody Fc-fragments. Respectively $C_{1/2}$ refers to the commonly used designation $C_{\alpha/\beta}$ (or $C_{\beta/\alpha}$) or $C_{\gamma/\delta}$ (or $C_{\delta/\gamma}$) in the context of T-cell receptors.

For the present invention the introduction of novel disulfide bonds (or disulfide- or sulphur-bridges) into the scARC is preferred as such bonds are automatically formed between the SH groups of the side chain of cysteines that are in close proximity during protein maturation in the endoplasmatic reticulum. The disulfide bond is a strong, covalent bond having a dissociation energy of 60 kcal/mole. A disulfide bond is about 0.2 nm in length, about 0.05 nm longer than a C—C bond. Rotation about the S—S axis is subject to a low barrier. Usually, disulfide bonds are formed by oxidation of two SH groups of two cysteines. Therefore, a sufficient redox potential has to be provided to allow the protein to form a disulfide bridge.

In one embodiment a scARC of the invention has one or more disulfide bonds, which link $V_1$ with $V_2$; and/or $V_{1/2}$ with $C_{1/2}$, such as $V_1$ with $C_1$, $V_2$ with $C_1$, preferably $V_1$ with $C_2$ or $V_2$ with $C_2$; and/or the Linker with $V_1$ or $V_2$. and/or the Linker with $C_1$ or $C_2$.

In a preferred embodiment a scARC of the invention has one or more disulfide bonds, which link $V_1$ with $V_2$; and/or $V_1$ with $C_2$; and/or $V_2$ with $C_1$; and/or the Linker with $V_1$ or $V_2$. and/or the Linker with $C_1$ or $C_2$. However, most preferred is a disulfide link between $V_1$ or $V_2$ with either a constant domain or the linker in order to reduce the degree of freedom of the variable domain and to reduce the chance that the link between the variable and the constant domain is broken, e.g. by proteolysis.

For the purpose of the present invention it is in another embodiment preferred that the disulfide bonds are artificially introduced, preferably wherein the one or more disulfide bonds have no equivalent in the native antigen recognizing molecule, such as a T-cell receptor or an antibody. The disulfide bond of the scARC of the invention is therefore preferably not present in the native scARC sequence from which the scARC of the invention is derived—and thus is artificially introduced. Most preferably, the disulfide bond in the scARC of the invention has no equivalent in any of the known ARC molecules.

Another embodiment relates to an scARC, wherein the one or more disulfide bonds are formed between the sulphur atoms of two cysteine residues, of which at least one is an amino acid substitution compared to the native sequence of the molecule. The scARC of the present invention is therefore derived from a native ARC sequence, into which cysteine residues are introduced at the relevant position in order to form a stable disulfide bond as described above. The introduction of cysteine residues is normally performed by site directed mutagenesis of the scARC coding nucleotide sequence. The codon for the amino acid to be substituted is then mutated such that it will code for a cysteine residue. Methods for site directed mutagenesis are known to the person of skill in the art, who also is aware that one must take caution not to introduce into the scARC sequence a frame-shift or a stop codon mutation. In the preferred situation the amino acid that is replaced with a cysteine is sterically similar to cysteine and thus is preferably selected from the group comprising serine, threonine and glycine.

In theory a direct linkage between the variable domain of the scARC, either in-between or with the constant domains, would be the most straight forward route for the design of a novel scARC of the invention. However, the desire of the invention is to provide functional antigen recognizing constructs. As the variable domains are key to the binding of the construct to the antigen, the design of the scARC requires the careful selection of the amino acid to be substituted in the native scARC sequence. Precaution must be taken not to interfere with the function of the variable domains and thus to remain in sufficient distance to the essential CDR3 loops in the variable domains. There is a restricted set of conserved amino acid residues described in TCR structure that are essential for proper folding and function (Chothia et al., 1988; Garcia et al., 1996), which should therefore be avoided in the design. However, particularly small, homologous conserved amino acid residues may tolerate a change to cysteine as long as the topology and antigen recognition of the construct is not impaired.

Preferred is therefore that the amino acid which is substituted with a cysteine in the scARC of the invention, is not essential for folding and/or function of the scARC, preferably wherein the side chain of the substituted amino acid is not directly involved in antigen recognition and/or not pointing to the interior of the domain where it is located. Hence preferred is that the side chain of the substituted amino acid in the variable domain is distant to the CDR1-3 loops, preferably at the base and/or the exterior of the variable domain.

The substitution of an amino acid residue in the native scARC sequence is to allow for a disulfide bond to be formed. Preferred is thus that the scARC according to the invention comprises cysteine residues which are substituted for amino acid residues whose main chain α-, or side chain β-carbon atoms are less than 0.65 nm, respectively 0.45 nm, apart. Such candidate amino acid residues are preferred as the disulfide bridge may only be formed within these constraints. Furthermore, The dihedral angle of $\chi_{ss}$ clusters is around +/−90°. Additionally, the $\chi^1$ of the formed cysteine adopt favourably between a +/−gauche or trans conformation, whereas $\chi^2$ dihedrals lie between a +/−gauche and rarely an +/−eclipse conformation. The sulphur-sulphur bond length should be around 0.2 nm (Sowdhamini et al., 1989; Voss et al., 1996).

A next embodiment of the invention relates to a scARC, wherein the scARC is partially or completely murinized in the constant domains. A "murinization" of the scARC plus $C_\alpha$ means that corresponding amino acid exchanges, as present in the mouse-constant domain of said construct, are transferred into the constant domains of the scARC plus $C_\alpha$. In the maximal case, the constant domains of the scARC plus $C_\alpha$ are replaced by murine domains. In general, as many murine exchanges are introduced into the constant domain as are required for the effective competitive replacement of the endogenous $TCR_\alpha$ chain and the $C_\alpha$-construct. The person of skill is readily able to determine and to define the number of exchanges that is effective in the respective case. These exchanges are found in both recombinant constructs, since they shall promote the specific pairing. It is possible to also introduce xenogenic, that is, in comparison with the human sequence foreign-species, point mutations that differ from the mouse-sequences, but that provide for a comparable positive effect on the preferential interaction of the TCR and their incorporation into the CD3-complex.

It is also possible that scARCs of human origin are employed, which, nevertheless, have been modified so strongly in the variable antigen-recognizing domains thereof, for example through affinity maturation, such as phage display or other interventions, that these are to be designated as merely of original-human origin. It is also possible that scARCs from other species (in general mammals) are used that are strongly modified through sequence-modifications and are suitable for the clinical use. Thus, the term "xenogenic" amino acid exchanges in the constant domains generally designates species specific differences between variable and constant domains.

Preferably a scARC according to the invention is an scARC provided with additional (functional) domains or an scARC provided with alternative domains, e.g. an scARC provided with a different transmembrane-domain as membrane anchor. Furthermore encompassed are scARC fusion proteins, composed of the antigen recognizing scARC portion and a second effector portion. Conceivable in this context is for example the fusion of an inventive scARC to human IL-2 or IgG1, as described before in Zhu et al., 2006.

For the herein described invention is preferred that the scARC is an antibody single chain Fv fragment (scFv) or a single chain T-cell receptor (scTCR), specifically wherein the scTCR is preferably a alpha/beta TCR or a gamma/delta TCR.

In the embodiments of the present invention wherein the scARC is a scFv, the scFv comprises the domains $V_L$-Linker-$V_H$-$C_H$ or $V_H$-Linker-$V_L$-$C_L$, and in the embodiments wherein the scARC is a α/β scTCR, the scTCR comprises the domains $V_\alpha$-Linker-$V_\beta$-$C_\beta$ or $V_\beta$-Linker-$V_\alpha$-$C_\alpha$.

One preferred embodiment relates to an scFv fragment stabilized according to the present invention, wherein the scFv fragment recognizes the tumor antigen ErbB2 (Her2/neu), which was previously shown to be effective as a classical CD3ζ-"T-Body"-fusion construct scFv(FRP5)-$C_\beta$/$C_\alpha$ (Uherek et al., Blood 2002, 100 1265-1273). For this it is preferred that the scFv fragment is fused to a constant domain, in a similar fashion as for the scTCR construct, preferably a murinized $C_\beta$-domain. Such a construct may then be expressed in connection with the heterodimeric constant domain, e.g. $C_\alpha$. The concept of scFv based scARC is also known as single chain chimeric antigen receptor (scCAR).

Preferred is that the scARC is of mammalian origin in the variable domains, or is of original mammalian origin, preferably of human origin. Specifically in the context of murinization as described herein above, a scARC is of non-murine origin, preferably non-murine mammalian origin. Most preferred is a original human scARC.

In the context of the present invention "murinization" shall encompass the introduction of the corresponding murine amino acid in the scARC of choice, which might be, for example, a goat, rabbit or preferably a human scARC. However, furthermore, a murinized scARC may be obtained by providing a murine scARC, e.g. a murine constant domain, into which the corresponding amino acids of another species are introduced. For example, the murine scARC or domain is modified such that the corresponding human amino acids are introduced, therefore "humanizing" the original murine sequence. The same strategy may be employed with any other species.

The scARC molecules according to the present invention may be expressed on the cellular surface of a host cell. To this end a nucleic acid construct encoding the scARC of the invention is introduced into a suitable host cell to allow the expression and surface transportation of the scARC. Suitable host cells are preferably cells of the immune system, most preferably T cell or a Natural Killer (NK)-cell, NKT-cell, CD4+T-Helper-cell, CD8+ cytotoxic T-cell, regulatory T-cells, a T-cell hybridom or a Jurkat T-cell.

Another embodiment of the invention describes a scARC as a soluble molecule or a scARC coupled to a solid matrix. Such a scARC is in one embodiment preferably a multimerized scARC, therefore is provided as a plurality of scARC molecules, like dimmers, trimers and tetramers, preferably wherein the scARCs are of the same kind. The multimerized scARC of the invention is provided in a further embodiment on a matrix surface or as a particle, or associated to a lipid bilayer or monolayer as a liposome structure or a vesicle.

The soluble scARC of the invention may be a scARC wherein the constant domain is coupled to a linker to allow the binding of the scARC-linker complex to a particle matrix or to a solid matrix. To this end, in a first embodiment the linker in this context my be a covalent bond between the scARC of the invention and the matrix. However, in order to link the scARC of the invention to a matrix particle or matrix surface, any kind of link, covalently or otherwise, may be employed. A preferred linker molecule of the invention is biotin which allows the binding to a matrix composed of avidin, such as streptavidin, neutravidin, extravidin. In a preferred embodiment of the invention the scARC is biotinylated, for example in its constant domains. A biotinylated scARC may than be bound to an avidin particle, preferably to a streptavidin particle, or an avidin solid matrix.

Suitable structures for use in the invention, for forming complexes with one or a plurality of scARCs, include membrane structures such as liposomes and solid structures which are preferably particles such as beads, for example latex beads. Other structures which may be externally coated with scARC molecules are also suitable. Preferably, the structures are coated with scARC multimers rather than with individual scARC molecules.

In the case of liposomes, the scARC or multimers thereof may be attached to or otherwise associated with the membrane. Techniques for this are well known to those skilled in the art.

Also preferred is the coupling of the scARC to another moiety. A label or another moiety, such as a toxic or therapeutic moiety, may be included in a multivalent scARC complex of the present invention. For example, the label or other moiety may be included in a mixed molecule multimer. An example of such a multimeric molecule is a tetramer containing three scARC molecules and one peroxidase molecule. This could be achieved by mixing the scARC and the enzyme at a molar ratio of 3:1 to generate tetrameric complexes, and isolating the desired complex from any complexes not containing the correct ratio of molecules. These mixed molecules could contain any combination of molecules, provided that steric hindrance does not compromise or does not significantly compromise the desired function of the molecules. The positioning of the binding sites on the streptavidin molecule is suitable for mixed tetramers since steric hindrance is not likely to occur.

It was shown that the correct surface expression of a scTCR on a host cell is dependent on the presence of the missing constant domain (Voss et al., 2010). Therefore in a further embodiment of the invention the scARC as described herein is present in a complex with the respective heterodimeric constant domain $C_1$ or $C_2$.

The variable domains of the scARC of the present invention are covalently connected by a short peptide, a "linker", whereby one of both constant domains is omitted. Hence, the linker of the present invention must have a suitable length so that the variable domains of the inventive scARC can pair without any sterical hindrance. On the other hand extensive linker length should be avoided in order to minimize any interference of the linker's side chains with the antigen recognition function of the variable domains. Thus, a further aspect of the present invention relates to a scARC according to the invention, wherein the linker (Li) is selected from $Li(Gly_4Ser)_3$, Li218, and LiSL7. Nevertheless, also other suitable linkers can be used, since the scARC according to the invention is not limited to the linkers as mentioned here.

Yet further preferred is in one embodiment that the scARC of the invention recognizes an antigen. Most preferably the antigen is selected from disease-specific surface-antigens, such as, for example, tumor associated antigens (TAA) or infection-specific surface-antigens, such as, for example, HIV-specific surface-antigens or CMV-specific surface-antigens. Antigens that are encompassed by the present invention are listed in Cheever et al., (Clin. Cancer Res., 2009, 15(17), 5323-5337).

A preferred scARC according to the invention is a gp100 (280-288)-specific scTCR, WT1(126-134)-specific scTCR or a Cytomegalovirus (CMV) pp65(495-503)-specific scTCR. The gp100 (280-288)-specific scTCR in one embodiment has at least one disulfide bond formed by a pair of amino acid substitutions selected from the group consisting of $V_\alpha$ G49C and $V_\beta$ G121C, $V_\alpha$ G121C and $V_\beta$ G49C, $V_\alpha$ L46C and $C_\beta$ P82C, $V_\alpha$ G49C and Linker G16C, $V_\alpha$ G49C and Linker G17C and $V_\alpha$ G49C and Linker G18C.

The indicated amino acid positions refer to the dedicated topological numbering of TCR V- and C-domains of the IMG database (Lefranc, 2003; Lefranc et al., 2005). The nomenclature refers both to the amino acid positions within the domains of a TCR and antibody domains.

In a most preferred embodiment the gp100 (280-288)-specific scTCR is the scTCR known from Voss et al. 2010. Therefore, part of the present invention is a gp100 (280-288)-specific scTCR as in Voss et al. 2010 with the above amino acid substitutions. It is further preferred that this scTCR harbours also the artificial disulfide bond scTCR S79C/Mu $C_\alpha$ T84C to efficiently link the co-expressed $C_\alpha$-domain with the scTCR (Kuball et al., 2007).

For the skilled person it is comprehensible that the principles of the scARC design and of the inventive scARCs as described herein above apply both to T-cell receptor based constructs as well to scFv fragment based constructs, also known as the "T-body" design.

The object of the present invention is also solved in a second aspect by a scARC particle, comprising at least one scARC as described herein above. The scARC particle is thus preferably biotinylated in the constant domain and bound to an streptavidin particle via the interaction between biotin and streptavidin, preferably to form a multimeric scARC particle A third aspect of the present invention relates to a method for producing a stabilized functional scARC, comprising
  a. providing of a suitable host cell,
  b. providing at least one genetic construct encoding for a scARC according to any one of claims 1 to 21,
  c. optionally, providing a genetic construct comprising the respective heterodimeric constant domain $C_1$ or $C_2$,
  d. introducing directly or indirectly the genetic construct/s via viral or non-viral gene transfer into the host cell, and
  e. expressing the genetic construct of the scARC-fragments by the cell.

In one embodiment the above method comprises further the presentation of the stabilized heterodimeric scARC by the cell.

Another embodiment of the aforementioned third aspect further relates to a method, wherein said host cell is a mammalian, in particular a human cell. Most preferred is further that the cell is not a human embryonic stem cell. Preferred cell types according to the invention are selected from immune cells, such as a T-cell or a NK-cell, NKT-cell, CD4+T-Helper-cell, CD8+ cytotoxic T-cell, regulatory T-cell, a T-cell hybridom or a Jurkat T-cell. For the present invention any cell is preferred which allows for a stable and correct surface expression of the scARC of the invention, specifically wherein the during the protein maturation process within the cells the correct disulfide bonds are formed.

The genetic construct encoding for the scARC of the present invention may be selected from any suitable nucleic acid construct that allows for the introduction and expression of nucleic acids in a host cell. Such molecules are for example DNA vectors that are transfected into the host cell, either by electroporation, or for example based on a liposomal transfection system. Also viral transduction systems are well known in the art and may be employed in context of the present invention to introduce the genetic construct into the host cell.

A next embodiment relates to the above method, wherein said scARC is co-expressed in the orientation signal-peptide (SP)-V1-Linker-V2-C2 together with the constant domain SP-C1, or the scARC is co-expressed in the orientation SP-V2-Linker-V1-C1 together with the constant domain SP-C2.

In a preferred embodiment of the invention both scARC-fragments are localised on one genetic construct. This allows for the expression of the scARC and the heterodimeric $C_1$ or $C_2$ domains in a 1:1 stoichiometry.

The above method may in one embodiment further comprise the purification of the scARC from the host cell and, optionally, the reconstitution of the translated scARC-fragments in a T-cell.

Thus, in a fourth aspect the present invention further provides a recombinant cell line, produced according to a method as described herein above. The cell according to the invention is characterized in that it contains the genetic construct for the scARC to be expressed and/or shows surface expression of the scARC of the present invention.

In a fifth aspect a stabilized scARC, produced with the method as described above is provided.

In a sixth aspect, an isolated nucleic acid encoding for a scARC according to the invention is provided. Preferably the isolated nucleic acid according to the invention is comprised in a DNA or RNA-vector molecule to allow for the expression of said isolated nucleic acid molecules in a host cell.

The object of the present invention is also solved in a seventh aspect by providing a pharmaceutical composition comprising a scARC, a scARC particle, a recombinant cell, in particular a recombinant T-cell, a nucleic acid or a DNA or RNA-vector molecule according to the embodiments of the herein described invention.

In an eighth aspect the invention relates to the use of a scARC, a scARC particle, a recombinant cell, in particular a recombinant T-cell, a nucleic acid or a DNA or RNA-vector molecule according to the embodiments of the herein described invention, for producing therapeutics and/or prophylactics for a treatment of a cancerous or infectious disease.

In one embodiment the above use is preferred, whereby a cancerous disease is treated that is related to a modified expression of MDM2, p53, Her-2/neu, Ras, tyrosinase, MART, gp100, MAGE, BAGE, MUC-1, TRP-1, TRP-2, CD45, CD19, WT-1, NY-ESO-1, PSA, hTERT, FLT3 or PRDI-BF1.

In a ninth aspect of the invention relates to the use of a scARC or a scARC particle of the invention for the visualization and/or quantification of the presence of an disease associated antigen, specifically for use in the diagnosis of a cancerous disease or infectious disease.

In a last aspect of the present invention a method for producing a stabilized scARC according to the invention is provided, the method comprising the steps of (1) providing a nucleic acid sequence encoding for a native ARC to be stabilized, (2) providing a three dimensional structure of the native ARC to be stabilized, (3) identifying in the three dimensional structure of the ARC at least one amino acid that qualifies for a substitution to cysteine, (3) introducing a mutation into the nucleic acid sequence encoding for a native ARC to be stabilized that substitutes said at least one amino acid that qualifies for a substitution to cysteine with a cysteine in the translated sequence of said nucleic acid, and thereby obtaining a nucleic acid sequence encoding for a modified ARC (4) expressing the modified ARC in a suitable host cell.

For the present invention the ARC may be selected from any antigen recognizing molecules which are described herein for the generation of a inventive scARC. Specifically preferred are TCRs or antibody fragments, either in double chain or single chain format. For the design of the novel disulfide bonds it is not essential whether the ARC to be modified is already in the dc or sc format. For example, to obtain a new and stabilized scTCR, the person of skill might identify suitable amino acid residues for cysteine substitution in the native ARC sequence and introduce the substitution into the sequence of a scARC derived from said native ARC.

The three dimensional structure of the ARC to be stabilized is preferably a protein structure, derived from X-ray crystallography, a method that allows one to measure the 3D density distribution of electrons in the protein (in the crystallized state) and thereby infer the 3D coordinates of all the atoms to be determined to a certain resolution. Also encompassed are structure obtained with Nuclear Magnetic Resonance (NMR) techniques.

The most important constraints for the selection of the suitable amino acid substitution are already described herein above and in the examples section. It is further preferred that the cysteine substitution of the at least one amino acid that qualifies for a substitution to cysteine results in the formation of a novel disulfide bond in the protein structure of the modified ARC. Usually it is preferred that at least two cysteine substitutions are introduced into the ARC sequence with the above method. "Novel" in the context of the present invention should be understood such that the disulfide bond was not formed in the native ARC sequence that is used to derive the scARC or modified ARC of the present invention. Most preferred is that the newly introduced disulfide bond did not exist in any known ARC.

The person of skill in the art is aware that the above described preferred embodiments of the invention may be, were appropriate, combined with each other. In particular it is clear to the person of skill that the modifications or preferred embodiments described for scTCRs also apply for scFv based constructs, or that the preferred embodiments described in the context of the scARC of the invention as such, also apply for the described method for its production.

While the present invention has been described with specificity in accordance with certain of its preferred embodiments, the following examples serve only to illustrate the invention and are not intended to limit the invention within the principles and scope of the broadest interpretations and equivalent configurations thereof.

The invention is illustrated in the figures in which:

FIG. 1 shows that the displacement of the antigen-recognizing domain V1 in scARC by dissociation or proteolysis may lead to malfunction and mis-pairing of scARC.

FIG. 2 shows that mis-pairing of scTCRs with endogenous $TCR_\alpha$ takes place. Shown is the retroviral expression of scTCR gp100 in Jurkat-76 cells lacking endogenous TCRs.

FIG. 3 shows the introduction of novel disulfide bonds into scARC to strengthen the interaction of variable domains. The preferred categories of disulfide bonds I to III are explained in detail in the examples section below.

FIG. 4 shows that residual mis-pairing of scTCRs is prevented by novel disulfide bonds. Shown is the retroviral expression of scTCR gp100 in Jurkat-76 cells lacking endogenous TCRs in flow cytometry analysis (FACS).

FIG. 5 shows IFNγ-secretion (ELISA) of scTCR gp100 retrovirally transduced human T-cells against peptide-loaded K562-A2 cells in peptide titration.

FIG. 6 shows a FACS of the expression of TCR WT1 (126-134) retrovirally transduced in human T-cells.

FIG. 7 shows a chromium release assay of TCR WT1 (126-134) retrovirally transduced in human T-cells.

FIG. 8 shows a Tetramer staining of scTCR gp100 transduced T-cells. (A) scARC without novel disulfide bonds. (B) scARC with novel disulfide bonds.

FIG. 9 shows cytotoxic function by a 51-Cr release assay of scTCR gp100 retrovirally transduced human T-cells against peptide loaded-K562-A2 cells in peptide titration.

EXAMPLES

Example 1

Design of Novel Disulfide Bonds

For the present invention in silico visual inspection and rational design of a crystal murine and human TCR structure was used, taken from RCSB protein data bank (Piscataway, N.J.), the pdb-entries ITCR and 2VLM, respectively. From this, it initially became clear, that murine and human TCR structures are very homologous with very small root mean Square deviations in the low Angstrom (A) range. Therefore, the design of a novel disulfide bond should be easily applied to both TCR-species. This is particular important with respect to the fact, that the $scTCR/C_\alpha$ format (Voss et al., 2010) was only functional for chimerized, i.e. in the $C_{\alpha/\beta}$-domains murinized constructs in the past. Since a TCR structure is composed of four globular immunoglobulin-like folded domains linked by short loops, any designed disulfide bridge between any domains should be also easily transferable from double chain TCRs, for which empirical structures exist, to out proprietary $scTCR/C_\alpha$ format for that the inventors assume a very similar fold.

The most important constraints in designing a disulfide bond are the distances of the participating main chain $C_\alpha$- or side chain $C_\beta$-atorns that have to be smaller than 6.5 Å and 4.5 Å respectively. The dihedral angle of $\chi_{ss}$ clusters is around +/−90°. Additionally, the $\chi^1$ of the formed cysteine adopt favourably between a +/−gauche or trans conformation, whereas $\chi^2$ dihedrals lie between a +/−gauche and rarely an +/−eclipse conformation. The sulphur-sulphur bond length should be around 0.2 nm (Sowdhamini et al., 1989; Voss et al., 1996).

In theory, a direct linkage between both V-domains should be most straight forward in strengthening their interaction and thus their overall stability. However, the V-domains are in charge of recognizing the cognate antigen and any modification close to the antigen recognition moieties, particular the CDR3-loops, might interfere with function. In order to make the approach of the present invention applicable to a broad range of TCR subfamilies, and even to antibody scFv fragments, the inventors concentrated on rather small amino acid residues in V-domains that are stereochemically homologous to cysteine such as serine, threonine and also glycine. In the screen the inventors included both conserved and non-conserved amino acid residues. There is a restricted set of conserved amino acid residues described in TCR structure that are essential for proper folding and function (Chothia et al., 1988; Garcia et al., 1996). However, it was assumed, that particularly small, homologous conserved amino acid residues may tolerate a Change to cysteine as long as topology and antigen recognition are not impaired. The inventors decided to focus on residues that are predominantly located at the base and the exterior of the V-domains distant from the CDR1-3 loops and secondly, their side chains were not directly involved in antigen recognition and were not pointing to the interior of its domain.

The inventors identified 2 pairs of residues that obey the constraints mentioned above and that are topologically related by the pseudo-symmetric architecture of the TCR $V_\alpha/V_\beta$-heterodimer:

| I. $V_\alpha$ | strand | relative position | $V_\beta$ | strand | relative position |
|---|---|---|---|---|---|
| 1.) G49C | C' | N-terminally to CDR2 | GI21C | G | C-terminally to CDR3 |
| 2.) G121C | G | C-terminally to CDR3 | G49C | C' | N-terminally to CDR2 |

The identification of ideally suited residues to form a disulfide between V-domains is much more confined to few candidates as opposed to C-domains (Boulter et al., 2003) since the V-domains interface is not featured by a plane network of intimately interacting P-strands as it is the case for C-domains (Garcia et al., 1996). The twisted barrel-like architecture of those β-strands that approaches most closely to each other at the $V_\alpha/V_\beta$-interface comprising strands C and C' and strand F and G on either domain limits interaction to residues being part of strand C' and G. Notably, G49 is adjacent to P50, which is part of the conserved and tight P50/L50-interaction in many TCR and many more antibody-structures (Richman et al., 2009) and G121 is the C-terminal glycine of the conserved G×G-motif right after the highly variable CDR3-loop (Chothia et al., 1988).

As an alternative the inventors were seeking to link different domains to minimally impact on V-domains whose modification may interfere with their structure and function. The inventors noticed that $V_\alpha$ approximates $C_\beta$ via strand C and D, respectively, but not $V_\beta$ vice versa $C_\alpha$. Position 46 in $V_\alpha$ is not conserved and lies at the very end of strand C at the base of the V-domain. It equals a leucine in TCR gp100(280-288) and is located in a favourable position to the residue centered at position 82 of strand D in $C_\beta$. P82 is conserved in human and mouse C-domains. The hypothetical disulfide bond spans the global center of the 4-domain TCR molecule and should be accommodated there without sterical hindrance. In theory, fixation of $V_\alpha$ to $C_\beta$ should also strengthen the interaction of $V_\alpha$ to $V_\beta$.

| II. $V_\alpha$ | strand | relative position | $C_\beta$ | strand relative position |
|---|---|---|---|---|
| L46C | C | C-terminally to CDR1 | P82C | centre of D |

Additionally, the inventors intended to include the linker of the scTCR-concept. The artificial nature of this linker should not impair the native immunoglobulin-like folded structure of either $V_\alpha$ or $V_\beta$. The glycine/serine-rich composition of the flexible linker should easily tolerate a cysteine modification. Notably, the cysteine modification of a linker position may be attributed to an indirect modification of a V-domain provided that the modification is located at either end of the linker closely to the related V-domain. Since the C-terminus of a linker is more closely located to the $V_\alpha$-domain than its N-terminus to $V_\beta$ as deduced from crystal structures, it was decided to cysteine-modify the C-terminus of the linker and to find a potential cysteine binding partner on $V_\alpha$. The inventors chose G49C because this residue is located 'at the back' on the surface of the $V_\alpha/V_\beta$-structure where the linker was supposed to be settled. Moreover, from crystal structure this residue is not involved in antigen recognition or major stabilization of neither the $V_\alpha/V_\beta$-interface nor the TCR-structure at all. As the location of the linker was not exactly known due to missing empirical scTCR structures, positions G16, G17, and G18 of the 'SL7' 19 mer-linker (Robinson and Sauer, 1998) were mutated to cysteine. The inventors tested the middle G17C mutation initially to provide for a 'proof-of-concept'.

| III. $V_\alpha$ | strand | relative position | linker | strand relative position |
|---|---|---|---|---|
| 1. G49C | C' | N-terminally to CDR2 | G16C | at the 'back of a TCR', |
| 2. G49C | C' | N-terminally to CDR2 | G17C | close to strand C' on $V_\alpha$, |
| 3. G49C | C' | N-terminally to CDR2 | G18C | and strand G on $V_\beta$ |

The flexible (i.e. glycine and serine-rich) nature and abundant length (i.e. 19 mer) of the linker should allow for the formation of a disulfide bond without knowing exactly the stereochemical constraints of the chosen residues.

Figure 2:
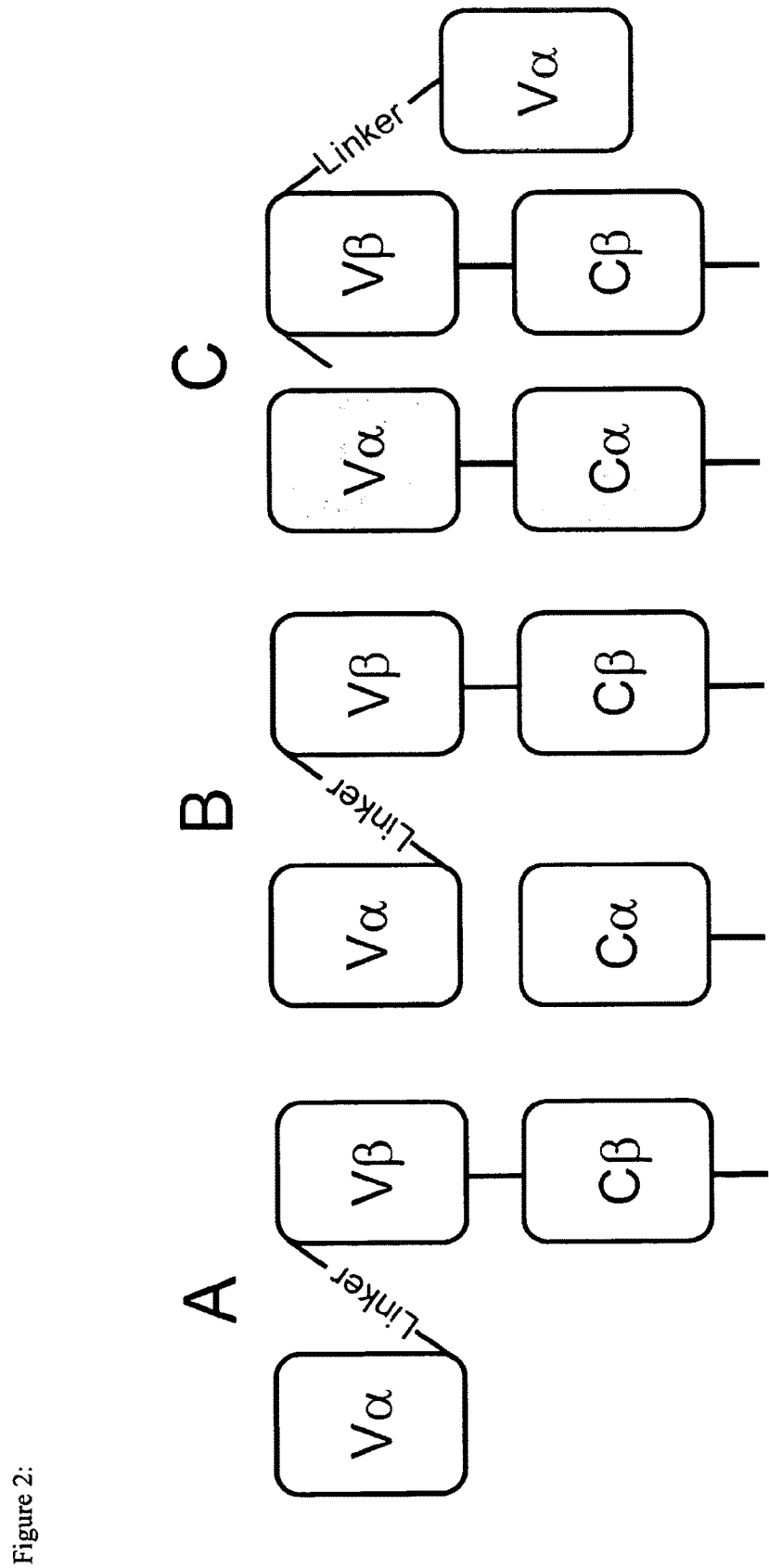
Figure 2:
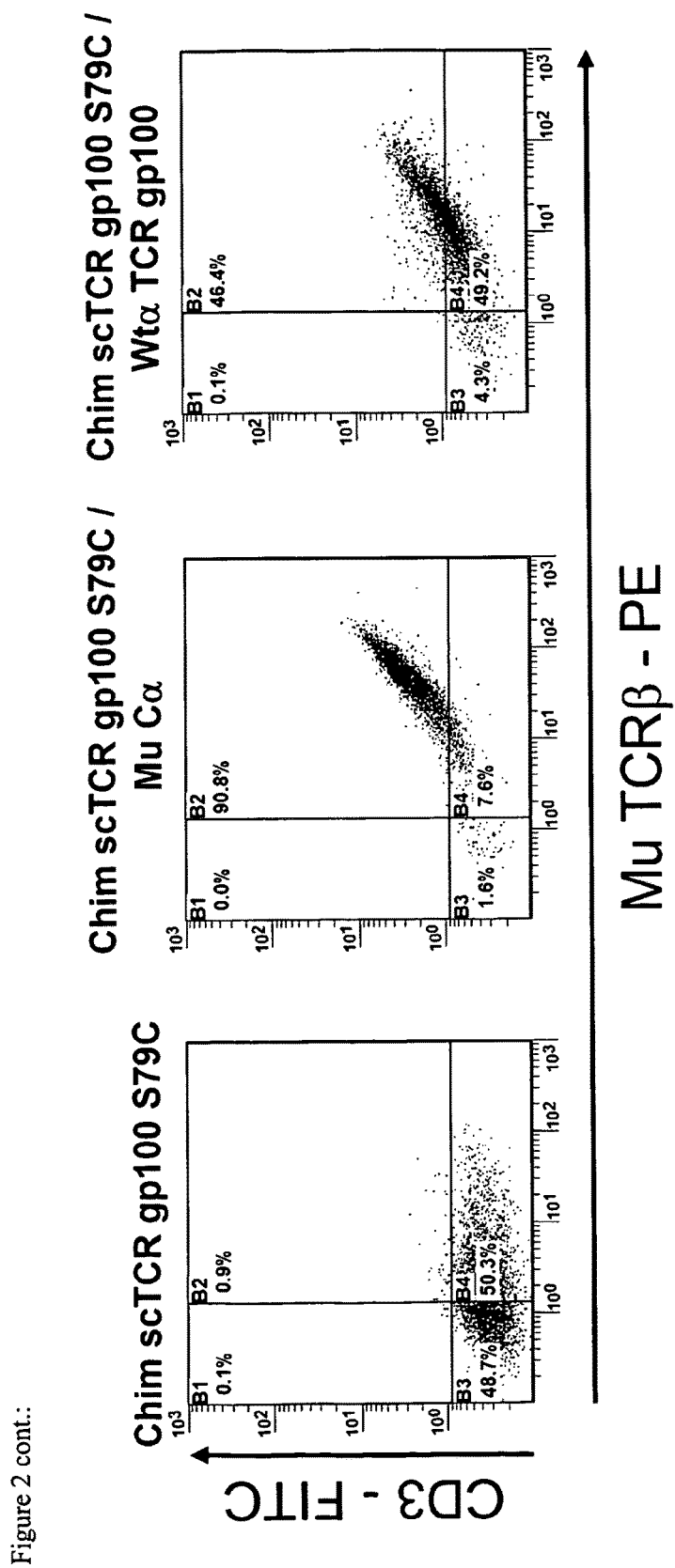
Figure 2:
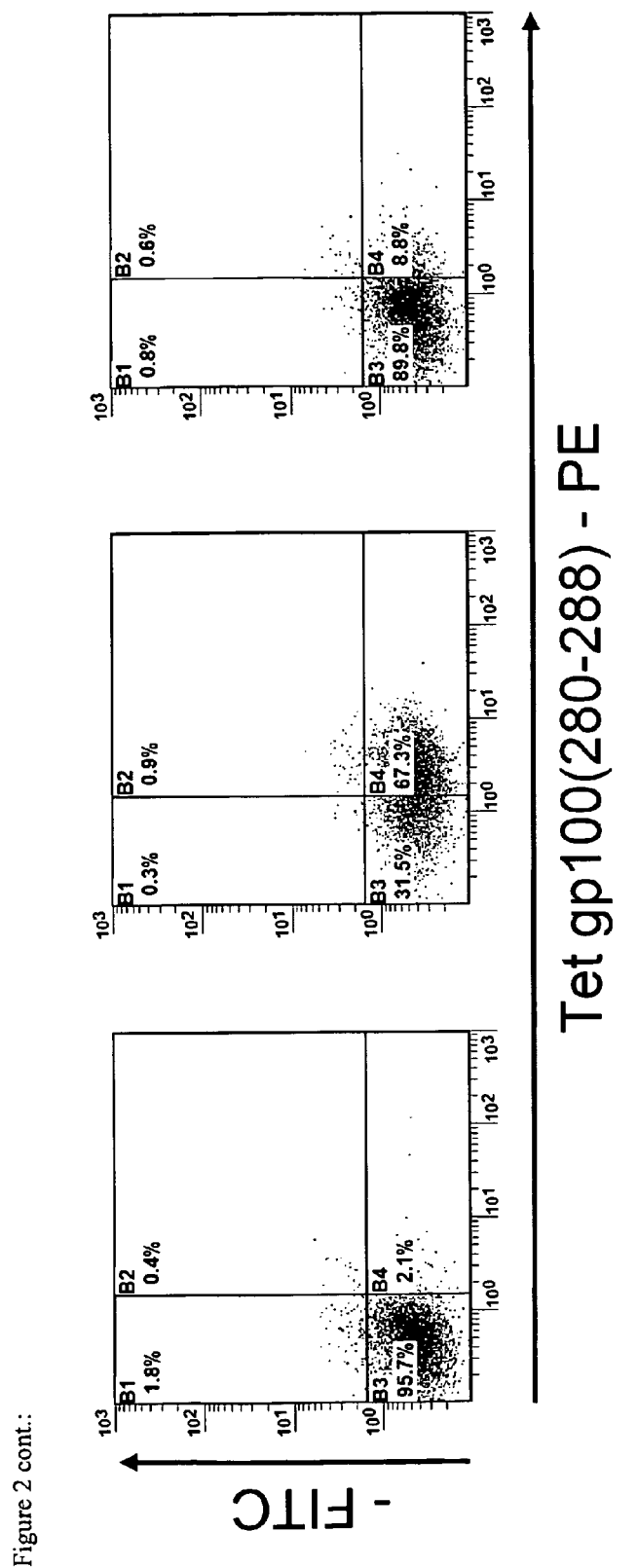

To provide for a proof of concept, the inventors introduced the amino acid residue replacements by site directed mutagenesis ('Quickchange mutagenesis'-kit, Agilent technologies) in a so-called chimerized, that means in C-domains murinized single chain TCR of the tumor associated antigen specificity gp100(280-288) (Voss et al., 2010). This scTCR harbored also the artificial disulfide bond scTCR S79C/Mu $C_\alpha$ T84C to efficiently link the coexpressed $C_\alpha$-domain with the scTCR (Kuball et al., 2007). This TCR, which served as the reference in all assays, is fully functional (FIG. 2B) when compared to the wild-type double chain TCR (Voss et al., 2010), but proved to be not entirely refractory to residual mis-pairing with arbitrary TCR$_\alpha$ chains (FIG. 2C).

The inventors also introduced the P46C/P82C-mutation linking $V_\alpha$ with $C_\beta$ into a chimerized, codon-optimized scTCR S79C/Mu $C_\alpha$ T84C specific for the TAA Wt1(126-134) (Xue et al., 2010). This scTCR proved to be non-functional in structural and functional avidity assays. The inventors were interested to verify, whether the introduction of a disulfide strengthening the interaction of $V_\alpha$ with $V_\beta$ would trigger any function in analogy to approaches that created the highly conserved P50/L50-interaction in hitherto non-functional scTCRs that naturally lacked this stabilizing interaction (Richman et ai., 2009).

The protocol of retroviral transduction, drug-selection to normalize TCR expression on a bulk T-cell level, and expansion was as outlined in (Voss et al., 2008). The inventors targeted primary T-cells that still coexpress endogenous TCRs in the presence of retrovirally introduced exogenous TCRs and alternatively, the leukemia T-cell line Jurkat-76, that are devoid of endogenous TCRs to study the occurrence of mis-pairing of any TCR combinations in the absence of endogenous TCRs that may interfere with them, in a more molecular and quantitative fashion (Voss et al., 2010).

Example 2

Verification of scARC Stability

Figure 3:
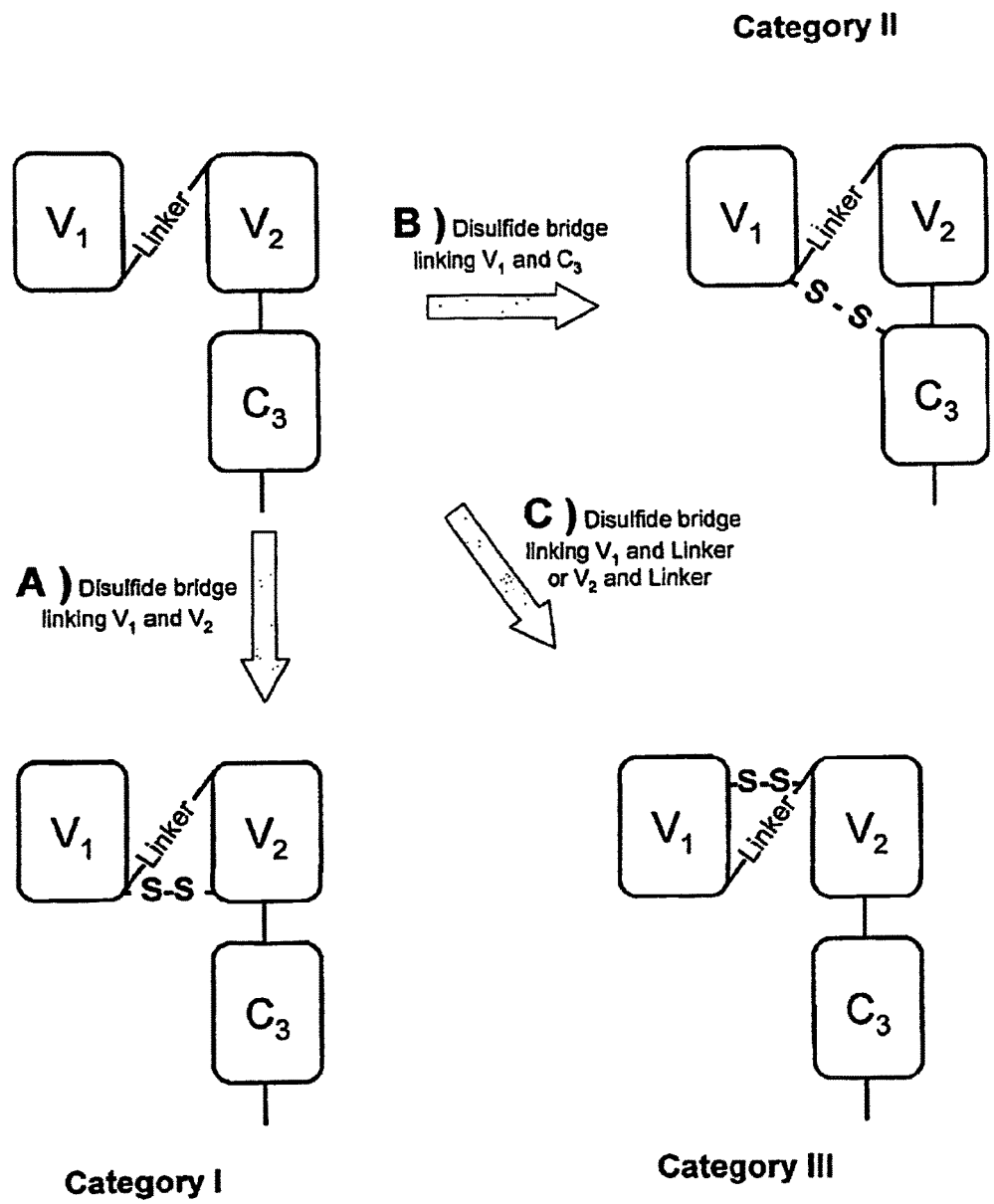

In FACS-analysis it turned out to be that the novel disulfide bonds of category I and II (FIG. 3A,B) slightly decreased expression of the scTCR/$C_\alpha$ (FIG. 4A,B left). Mis-pairing with full-length TCR$_\alpha$ gp100 serving as 'mimicry' endogenous TCR$_\alpha$ chain was almost abolished (FIG. 4A,B right). The disulfide bond of category III (FIG. 4C left) even improved expression of scTCR/$C_\alpha$ slightly, also in tetramer analysis (data not shown). This disulfide bond seems to protect the linker and thus, to stabilize the scTCR/$C_\alpha$-scaffold. However, tiny amounts of mis-pairing with TCR$_\alpha$ gp100 still took place as shown by CD3-expression on cell surface (FIG. 4C right) but in a much more reduced fashion when compared to the referenced scTCR (FIG. 2B). Tetramer staining was almost abolished and comparable to scTCR gp100 when expressed alone (FIG. 2A and data not shown). It is important to note that Mu TCR$_\beta$-staining is not a marker for functional surface expression of a TCR: A scTCR expressed alone without Ca can be detected on the cell surface by Mu TCRβ-staining, but turned out to be not functional (Voss et al., 2010).

Figure 5:
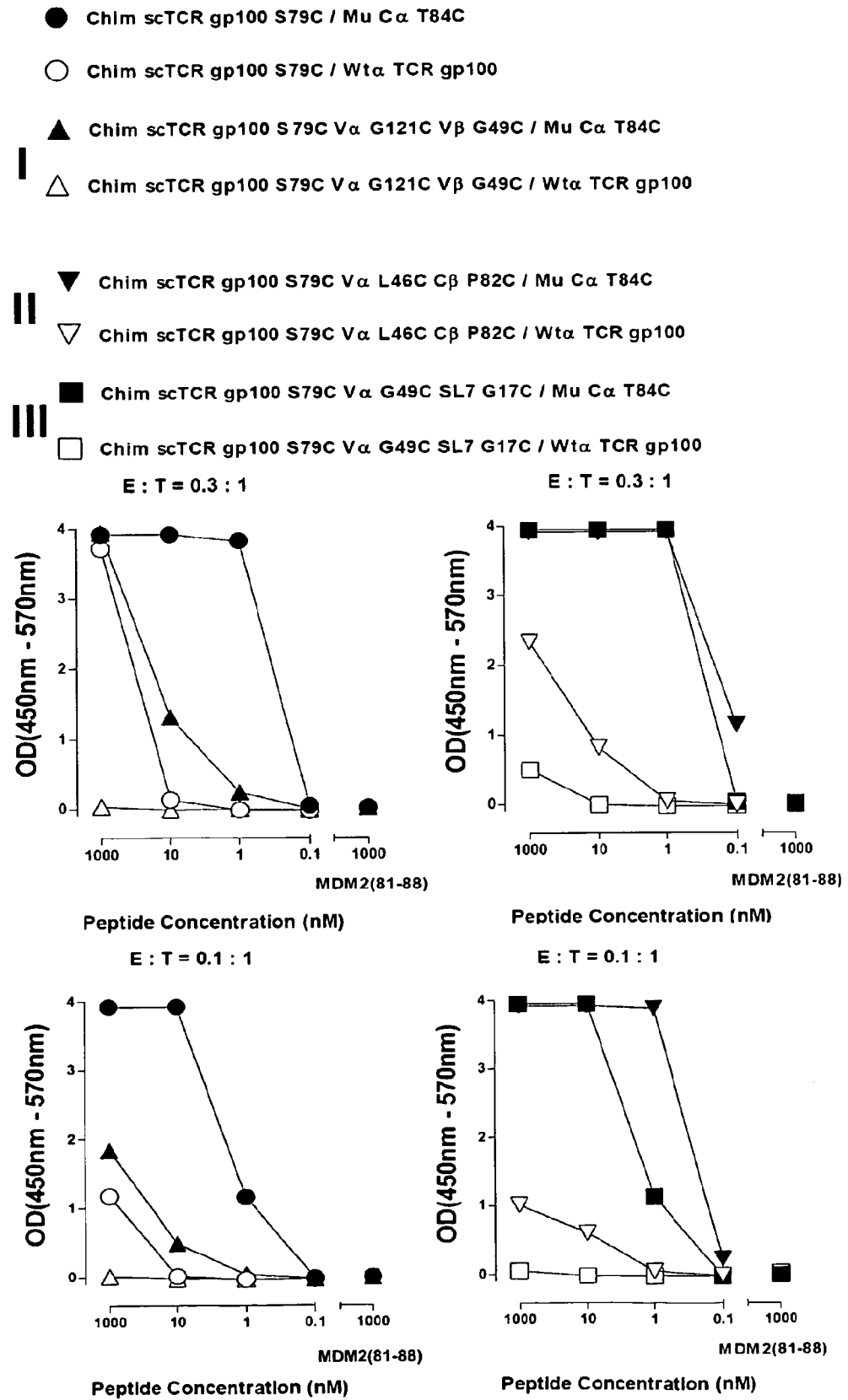

Functional avidities of TCR gp100-transduced T-cell were monitored by IFNγ-secretion ELISA (FIG. 5). Again, the disulfide bond of category III linking $V_\alpha$ with the linker demonstrated efficiency as high as the reference and significantly lower IFNγ-secretion activity when coexpressed with the 'mimicry' endogenous TCR$_\alpha$ gp100 chain. The disulfide bond-modified TCRs of category I and II elicited lower and higher IFNγ-production than the reference resulting in a higher and lower potential to prevent mis-pairing.

Figure 6:
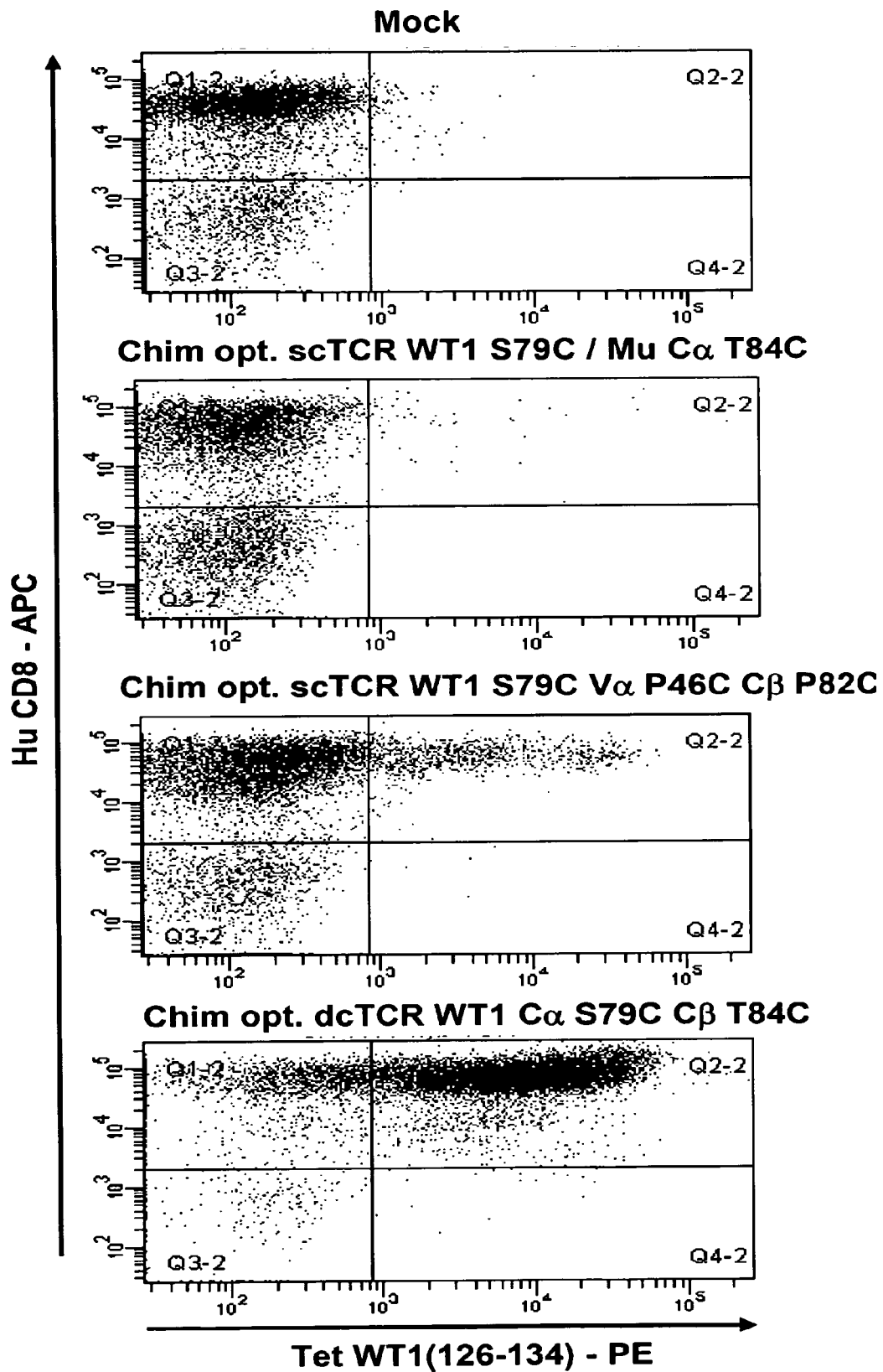

The inventors also designed a WT1-specific scTCR being coexpressed with $C_\alpha$. Surprisingly, this scTCR turned out to be non-functional in tetramer staining (FIG. 6) and cellular cytotoxic assays (data not shown). The inventors aimed at stabilizing this weak scTCR by introducing a disulfide of category II and observed tetramer-positivity after few rounds of T2*peptide-restimulations (FIG. 6). From tetramer-analysis, this scTCR was lower expressed than its reference, the chimerized (Chim), codon-optimized (opt.) and C-domain disulfide-linked ($C_\alpha$ T84C $C_\beta$ S79C) double chain (dc) TCR WT1. However, the former revealed substantial cellular cytotoxicity in chromium release assays when targeted against the leukemia cell line K562-A2 (FIG. 7) that endogenously overexpress WT1. K562, that were not transfected with HLA-A2, were not able to present the endogenously processed WT1(126-134)-peptide on the cell surface and thus, were merely recognized especially at low E:T-ratios. In Summary, the disulfide bond-modified scTCR WT1 proved efficiency and specificity.

Figure 4:
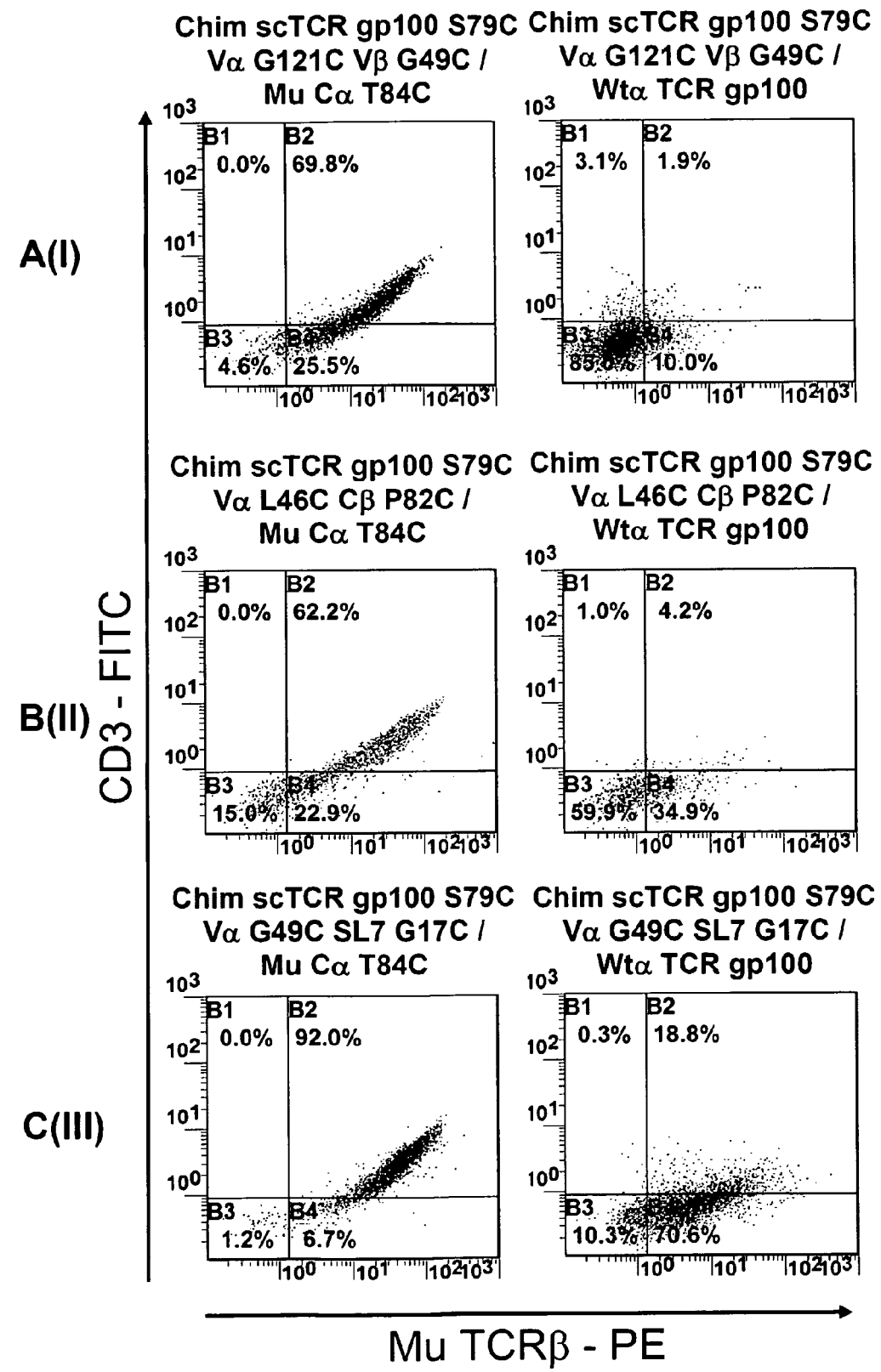
Figure 7:
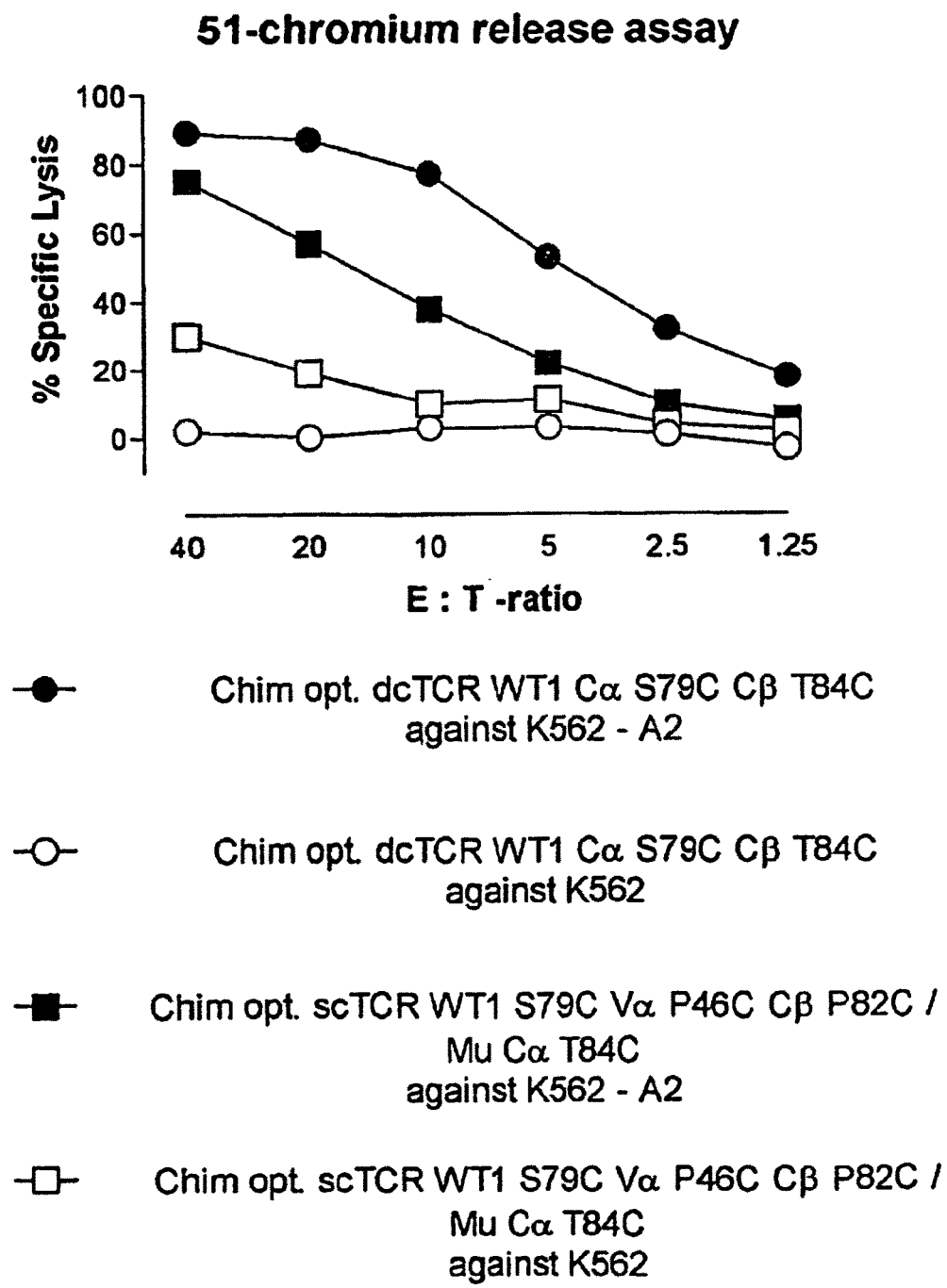

These experiments indicated, that the modeled disulfide bonds were formed and to various amounts sustained or even increased expression of the disulfide bond-modified scTCR (FIG. 4 left). Most notably, residual mis-pairing with $TCR_\alpha$ gp100 as a mimicry for an endogenous $TCR_\alpha$ chain was substantially prevented (FIG. 4 right). This is also true for their functional activity (FIG. 5). The disulfide bond of category III linking $V_\alpha$ with the linker seems to be superior to the other designed disulfide bonds because both effector function and the avoidance of residual mis-pairing were optimally accomplished. The introduction of a disulfide bond of category II, the only one tested for 'weak' scTCRs so far, is also able to initiate functionality of previously non-functional scTCRs (FIGS. 6 and 7).

Figure 8A:
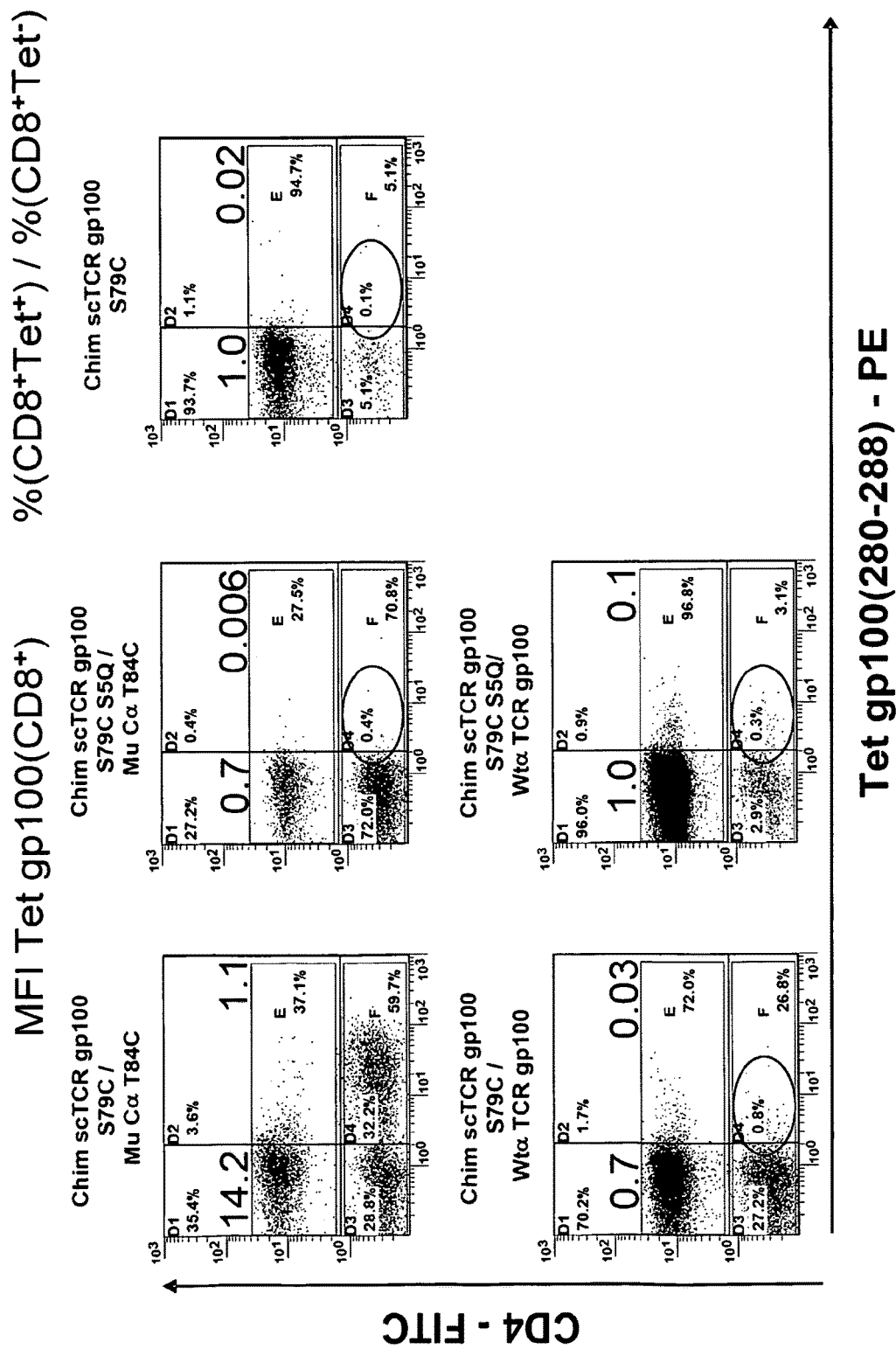
Figure 8B:
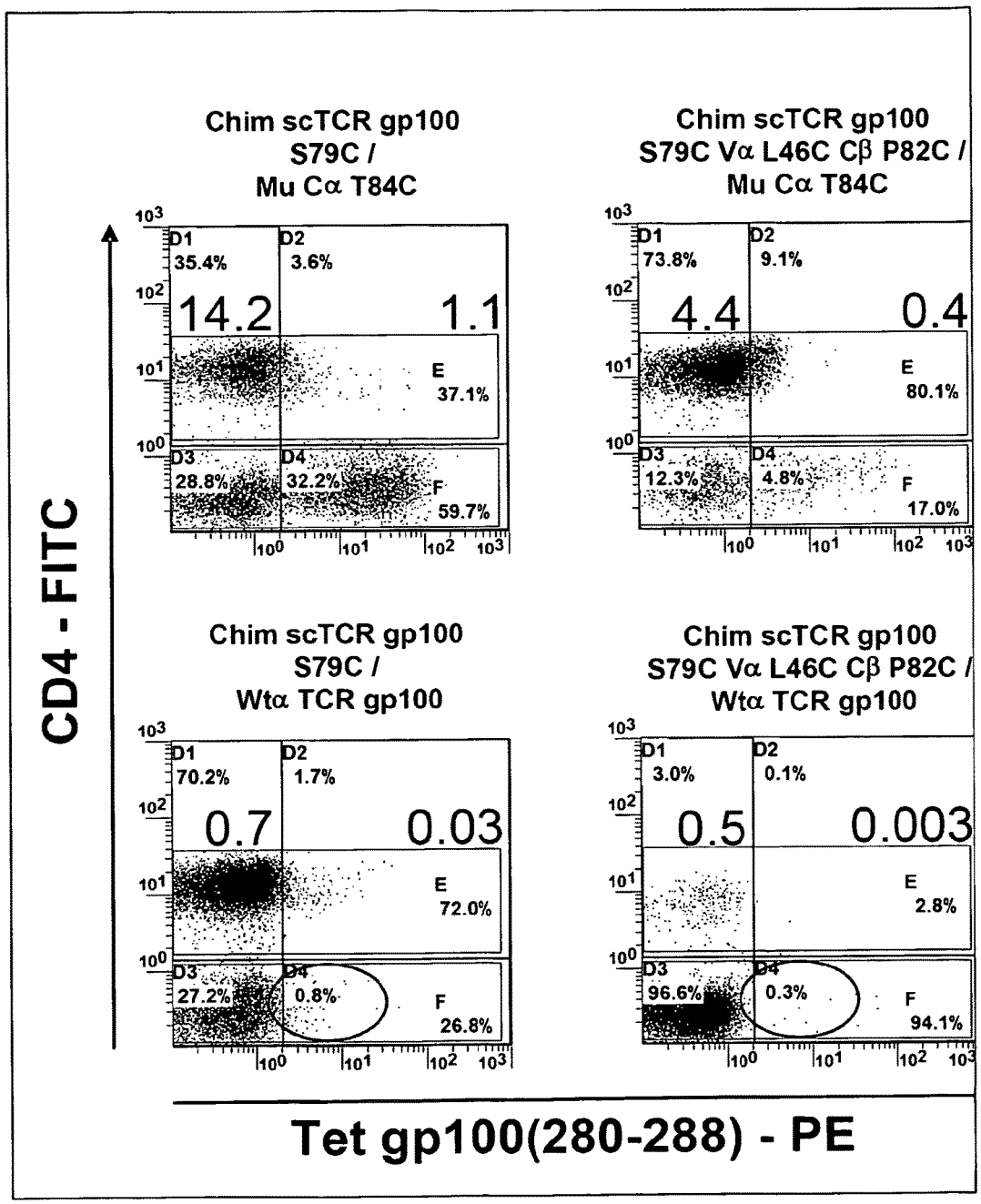
Figure 8B:
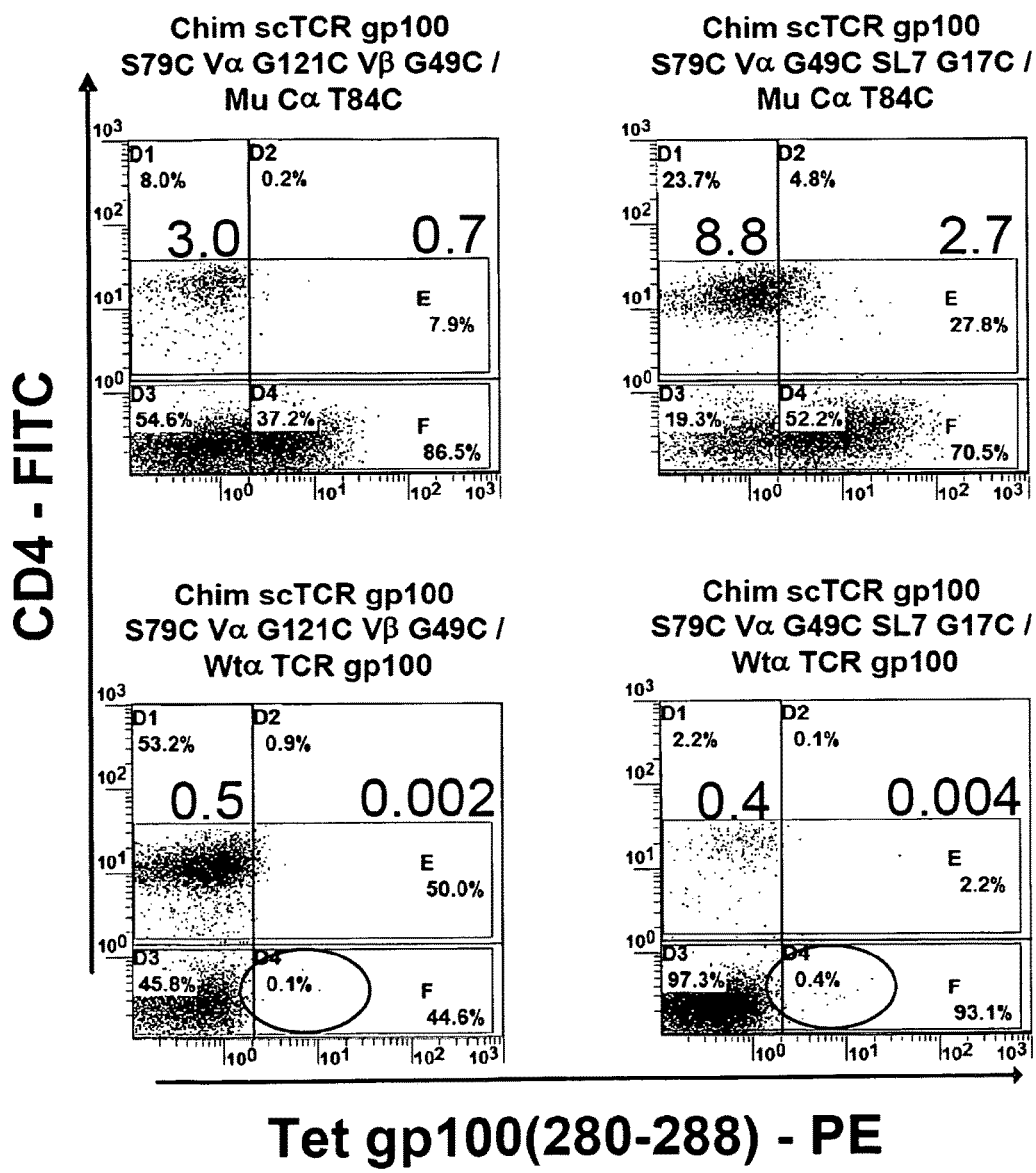

Tetramer-staining of human T-cells retrovirally transduced with different scTCR gp100 constructs revealed substantial residual antigen recognition when coexpressed with a "mimicry" endogenous $TCR_\alpha$ chain, the $Wt_\alpha$ TCR gp100 (FIG. 8). Thus, sterical hindrance of a scTCR gp100 did not entirely avoid mis-pairing with a full length $TCR_\alpha$ chain.

In both cases where an unmodified or CDR3a S5Q-inactivated scTCR gp100 were coexpressed with $Wt_\alpha$ TCR gp100 residual mispairing were evident (0.8% and 0.3%, respectively). In order to account for varying CD %/CD4-ratios in T-cell samples, we calculated a normalized CD8+ tetramer positivity by considering the ratio of tetramer positive and tetramer-negative cells (% (CD8+Tet+)/% (CD8+Tet−)). This yielded ratios for both mis-paired cases (0.03 and 0.1, respectively) slightly higher than the negative control Chim scTCR gp100 (0.02) indicating specific tetramer-staining above background. This proportion is quite low but taking into account the PBMC bulk transduction protocol of high numbers of human T-cells in envisioned clinical trials, this may cause severe side effects in undesignated antigen recognition.

The introduction of different disulfide bonds of categories I, II, or III, which in theory strengthen the interaction of scTCR $V_{\alpha/\beta}$-domains (FIG. 8B) demonstrated varying but substantial amounts of tetramer-positivity when coexpressed with the murine $C_\alpha$-domain. In particular, the introduction of an artificial disulfide bond between $V_\alpha$ and the carboxyterminus of the linker SL7 even increased the fraction of tetramer-positive T-cells (2.7) when compared to the reference Chim scTCR gp100 S79C/Mu $C_\alpha$ T84C (1.1) and led to a comparable mean fluorescence intensity (MFI) of CD8+ T-cells (8.8 versus 14.2). Conclusively, including data obtained from scTCR gp100-transduced Jurkat-76 (FIGS. 2, 4), disulfide bond-modified scTCR gp100 constructs apparently were not impaired in structure or were even stabilized by the $V_\alpha$/linker-modification.

When disulfide bond-modified scTCR gp100 constructs were coexpressed with the "mimicry" endogenous $TCR_\alpha$ gp100-chain the CD8+ ratio of tetramer-positive T-cells substantially dropped (0.003, 0.003, 0.004) at least 10-fold below the ratio of the unmodified (0.03) or inactivated (0.1) scTCR gp100 as references. This clearly confirmed the hypothesis that all designed disulfide bonds of categories I, II, and III efficiently prevented residual mispairing while sustaining their designated function.

Figure 9:
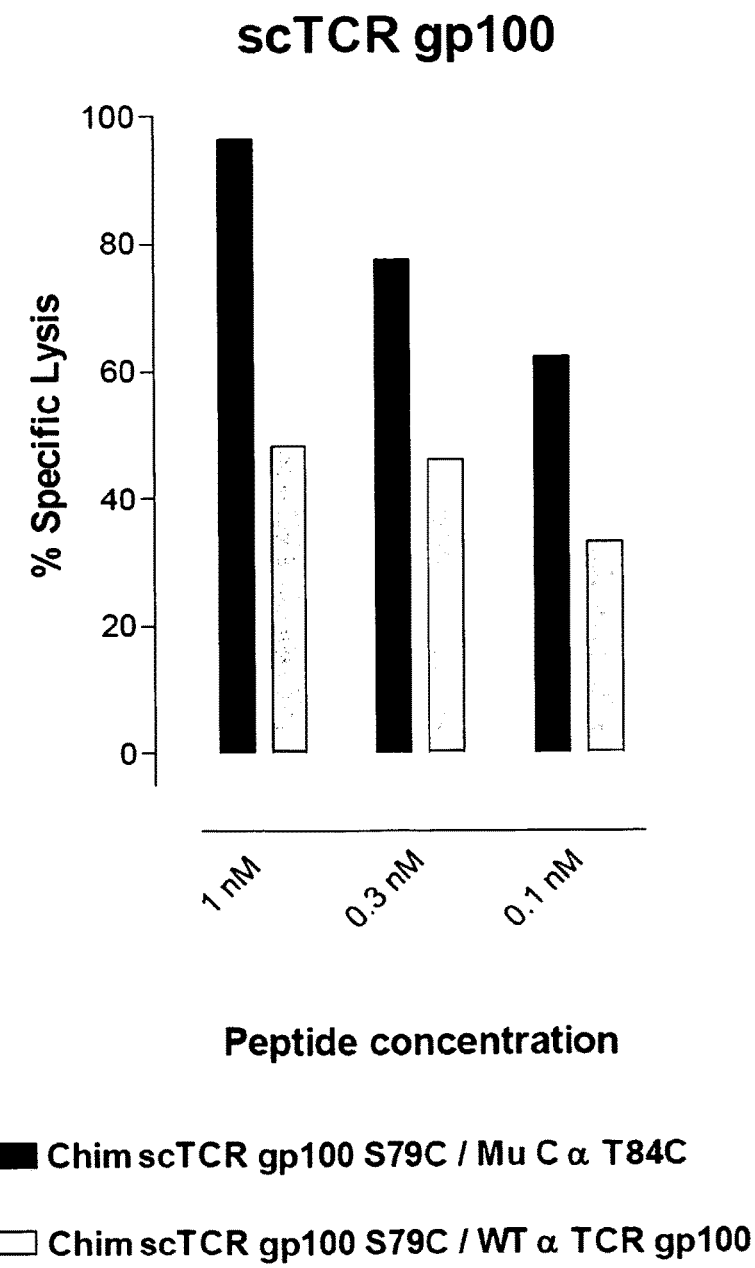
Figure 9:
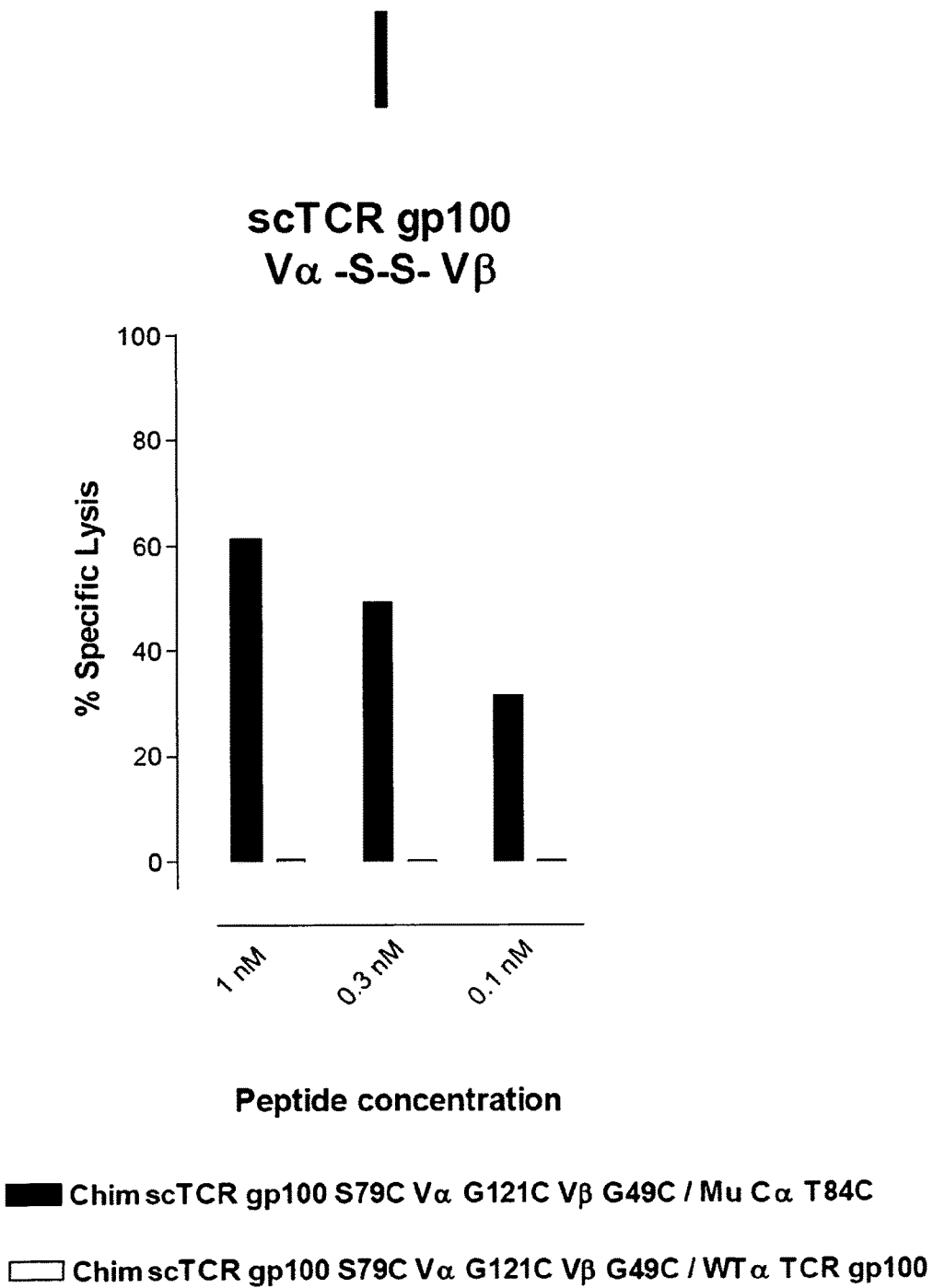
Figure 9:
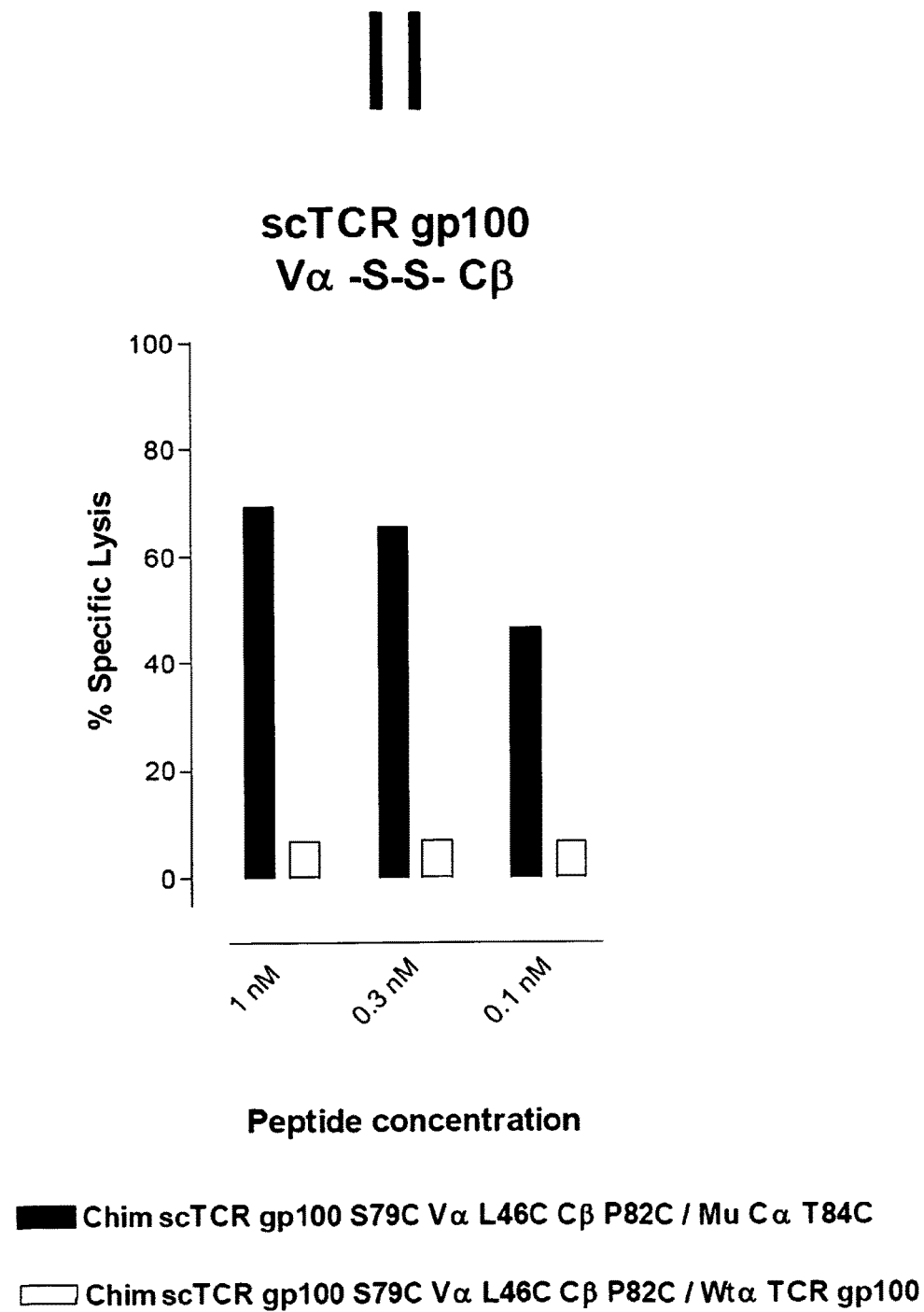
Figure 9:
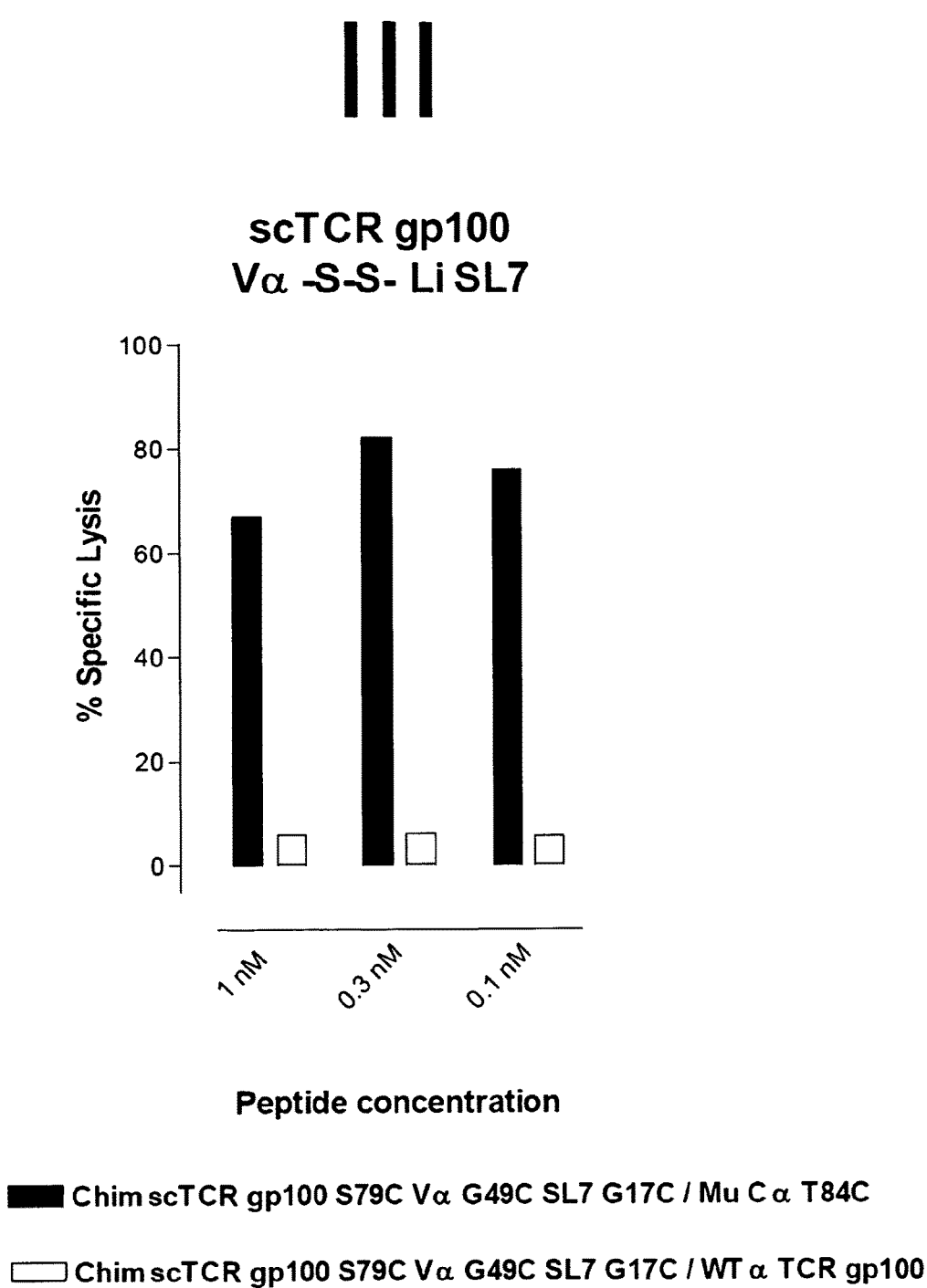

The inventors analysed the prowess of our concept to prevent cytotoxicity caused by mis-pairing in 51-chromium release assays (FIG. 9). For this, we quantified cytotoxic function around the range of half-maximal lysis efficiency of the reference Chim scTCR gp100 S79C I Mu $C_\alpha$ T84C (i.e. 0.1 nM peptide concentration). Again, scTCR gp100 constructs mispaired with "mimicry" wild type TCRa gp100 chains revealed substantial cytolytic function (light grey bar) when compared to the reference (dark grey bar).

Contrarily, in all cases of artificially disulfide-bonded scTCRs coexpressed with the mimicry TCR, gp100 chain cytotoxicity was significantly reduced and much lower than that of the related scTCR gp100 I $C_\alpha$ (dark coloured bars). In case of the modified scTCR gp100 linking $V_\alpha$ with the C-terminus of SL7, cytotoxicity is still on top at 0.1 nM peptide concentration, corroborating the stabilizing effect of this kind of disulfide bond on scTCR gp100/$C_\alpha$.

The invention claimed is:

1. A stabilized functional single chain antigen-recognizing construct (scARC), comprising TCR Vα and Vβ variable domains, and a TCR Cα or Cβ constant domain, said domains being covalently linked to one another as a $V_\alpha$-Linker-$V_\beta$-$C_\beta$ single chain or as a $V_\beta$-Linker-$V_\alpha$-$C_\alpha$ single chain, wherein the Vα and/or Vβ variable domains are structurally stabilized by one or more disulfide bonds between one or more pairs of cysteine amino acid residues, said disulfide bonds having no equivalent in a native αβ-TCR, and said pairs of cysteine amino acids residues naturally occurring at certain amino acids in said domains, or being substituted into certain amino acids in said domains, said amino acids occurring at positions selected from the group consisting of: at Vα position 49 and at the C-terminal glycine of the conserved GxG-motif occurring after the highly variable CDR3-loop of Vβ, at the C-terminal glycine of the conserved GxG-motif occurring after the highly variable CDR3-loop of Vα and at Vβ position 49, at Vα position 46 and at Cβ position 82, at Vα position 49 and at linker position 16, 17 or 18, the numbering of the Vα, Vβ and Cβ positions according to the nomenclature of the IMGT database.

2. The scARC according to claim 1, wherein said scARC is of human origin in the variable domains, and wherein the scARC is partially or completely murinized in the constant domains.

3. The scARC according to claim 1, wherein the scARC is a gp100 (280-288)-specific scTCR, WT-1(126-134)-specific scTCR or a Cytomegalovirus (CMV) pp65(495-503)-specific scTCR.

4. A scARC particle, comprising at least one scARC according to claim 1.

5. A method for producing a stabilized functional scARC, comprising:
   a. providing of a suitable host cell,
   b. providing at least one genetic construct encoding for scARC according to claim 1,
   c. optionally, providing a genetic construct comprising a heterodimeric constant domain $C_1$ or $C_2$, d. introducing the genetic construct/s into the host cell, and e. expressing the genetic construct of the scARC-fragments by the cell.

6. A recombinant cell line, produced according to a method according to claim 5.

7. An isolated nucleic acid encoding a scARC according to claim 1.

8. A DNA or RNA-vector molecule that comprises one or more nucleic acid(s) according to claim 7 and that can be expressed in cells.

9. A pharmaceutical composition comprising a scARC according to claim 1 and/or a nucleic acid encoding said scARC.

10. The scARC particle according to claim 4, wherein the at least one scARC is biotinylated in the constant domain and bound to a streptavidin particle via the interaction between biotin and streptavidin.

* * * * *